United States Patent [19]

Hoover

[11] Patent Number: 4,599,198

[45] Date of Patent: Jul. 8, 1986

[54] INTERMEDIATES IN POLYPEPTIDE SYNTHESIS

[75] Inventor: Dennis J. Hoover, Ledyard, Conn.

[73] Assignee: Pfizer Inc., New York, N.Y.

[21] Appl. No.: 780,353

[22] Filed: Sep. 26, 1985

Related U.S. Application Data

[63] Continuation of Ser. No. 762,099, Aug. 2, 1985.

[51] Int. Cl.$^4$ ................................................ C07K 5/06
[52] U.S. Cl. ................................. 260/998.2; 530/333
[58] Field of Search ................................. 260/112.5 R

[56] References Cited

U.S. PATENT DOCUMENTS 4,479,941 10/1984 Veber et al. ................ 260/112.5 R

OTHER PUBLICATIONS

Nicolaides et al., *Chemical Abstracts*, 68,7597, (1968), Abst. No. 78612z.

*Primary Examiner*—Delbert R. Phillips
*Assistant Examiner*—F. T. Moezie
*Attorney, Agent, or Firm*—Charles J. Knuth; Albert E. Frost; James M. McManus

[57] ABSTRACT

Bis(t-butoxycarbonyl) derivatives of phenylalanylhistidine as intermediates in the synthesis of rennin inhibiting polypeptides.

3 Claims, No Drawings

INTERMEDIATES IN POLYPEPTIDE SYNTHESIS

CROSS REFERENCE TO RELATED APPLICATION

This application is a continuation of copending application Ser. No. 762,099, filed Aug. 2, 1985.

BACKGROUND OF THE INVENTION

The proteolytic enzyme renin, which has a molecular weight of about 40,000, is produced in and secreted into the blood by the kidney. It is known to be active in vivo in cleaving the naturally-occurring plasma glycoprotein angiotensinogen, in the case of human angiotensinogen at the bond between the leucine (10th) and valine (11th) amino acid residues at the N-terminal end of the angiotensinogen:

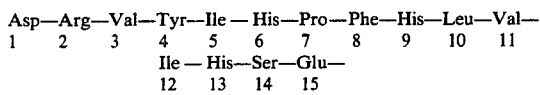

The circulating N-terminal decapeptide (angiotensin I) formed by the above cleaving action of renin is subsequently broken down by the body to an octapeptide known as angiotensin II. Angiotensin II is known to be a potent pressor substance, i.e. a substance that is capable of inducing a significant increase in blood pressure, and is believed to act by causing the constriction of blood vessels and the release of the sodium-retaining hormone aldosterone from the adrenal gland. Thus, the renin-angiotensinogen system has been implicated as a causative factor in certain forms of hypertension and congestive heart failure.

One means of alleviating the adverse effects of the functioning of the renin-angiotensinogen system is the administration of a substance capable of inhibiting the angiotensinogen-cleaving action of renin. A number of such substances are known, including antirenin antibodies, pepstatin and naturally-occurring phospholipid compounds. European Patent Application No. 45,665 (published Feb. 2, 1982) discloses a series of renin-inhibiting polypeptide derivatives of the formula X-Y-Pro-Phe-His-A-B-Z-W in which X may be hydrogen or an amino-protecting group, Y may be absent, B is a lipophilic amino acid residue, Z is an aromatic amino acid residue, W may be hydroxyl and A may be, inter alia,

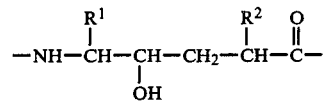

with each of $R^1$ and $R^2$ being a lipophilic or aromatic side chain. According to the definitions set forth in this published patent application, it is not contemplated that either A or Z could be statine or that B could be lysine.

European Patent Application No. 77,028A (published Apr. 20, 1983) discloses a series of renin-inhibiting polypeptide compounds having a non-terminal statine or statine derivative residue. Included within this series are compounds having a phenylalanine-histidinestatine sequence.

European Patent Application No. 132,304A also discloses the use of statine containing polypeptides as renin-inhibiting antihypertensive agents, and European Patent Application No. 114,993A discloses polypeptides containing cyclostatine, useful as renin-inhibiting antihypertensive agents.

SUMMARY OF THE INVENTION

It has now been found that certain polypeptides containing cyclostatine in which the structure of this aminoacid has been expanded in the carboxy portion of the molecule by an oxygen or nitrogen atom are useful as renin-inhibiting agents and have application in the treatment of hypertension and congestive heart failure.

This series of novel compounds consist of polypeptides and polypeptides derivatives of the formulae

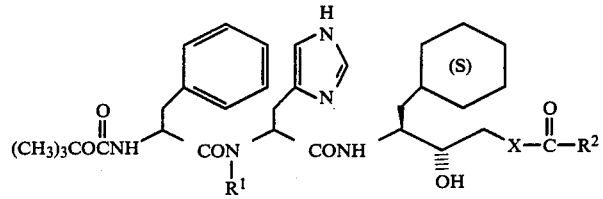

1

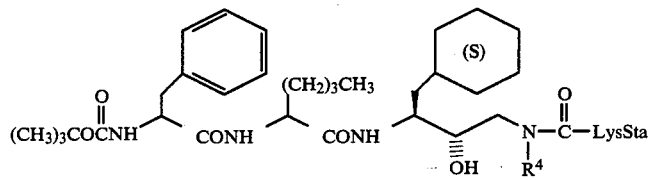

2 and a pharmaceutically acceptable salt thereof where $R_1$ is hydrogen or methyl; X is oxygen, amino, alkylamino of one to four carbon atoms, cyclohexylmethylamino, benzylamino, omega-aminohexylamino or methoxycarbonylmethylamino; $R_2$ is LysPhe, LysPhe methyl ester, LysPhe amide, LysSta, amino, alkylamino of one to four carbon atoms, alkyl of three to four carbon atoms, 4-imidazolylethylamino, omega-aminohexylamino, benzyloxy, omega-cyanopentylamino or a reduced IlePhe of the formula

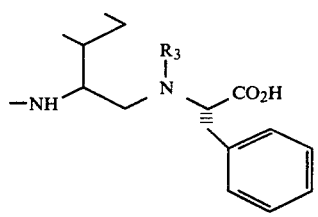

where $R_3$ is hydrogen, omega-aminohexyl or omega-cyanopentyl; and $R_4$ is alkyl of three to four carbon atoms.

Of particular interest are compounds of formula 1 where $R_1$ is hydrogen and X is oxygen. Especially preferred is the compound where $R_2$ is LysPhe.

Also of particular interest are compounds of formula 1 where $R_1$ is hydrogen and X is alkylamino of one to four carbon atoms. Especially preferred within this group are those compounds where $R_2$ is LysPhe and X is isobutylamino or isopropylamino, and where $R_2$ is LysSta and X is isobutylamino.

A third group of compounds of particular interest are those of formula 1, where $R_1$ is hydrogen and $R_2$ is a reduced IlePhe of the formula

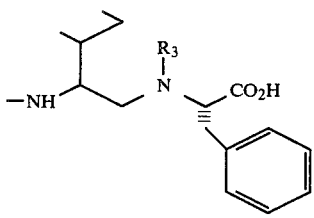

Preferred within this group of compounds are those where $R_3$ is hydrogen and X is oxygen, isobutylamino or amino and where X is isobutylamino and $R_3$ is omega-aminohexyl or omega-cyanopentyl.

Of particular interest are compounds of formula 2, where $R_4$ is alkyl of three to four carbon atoms. Especially preferred within this group is the compound where $R_4$ is isobutyl.

A compound of interest as an intermediate leading to the products of the instant invention is of the formula

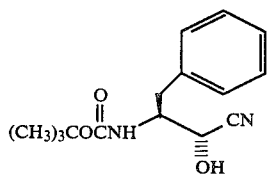

As previously indicated, the present invention embraces pharmaceutically acceptable salts of the biologically active compounds. Such salts are those which are non-toxic at the dosages administered. Since compounds of the invention may contain both basic and acidic groups, both acid addition and alkali addition salts are possible. Pharmaceutically acceptable acid addition salts include e.g. the hydrochloride, hydrobromide, hydroiodide, sulfate, bisulfate, phosphate, acid phosphate, acetate, lactate, maleate, mesylate, fumarate, citrate, acid citrate, tartrate, bitartrate, succinate, gluconate and saccharate salts. Pharmaceutically acceptable alkali addition salts include e.g. the sodium, potassium, calcium and magnesium salts. Conventional methods of forming acid addition and alkali addition salts may be employed.

In the interest of brevity, the commonly accepted abbreviated name of the individual aminoacids have been employed where possible. For example, the amino acid phenylalanine is abbreviated as Phe, histidine as His, lysine as Lys, statine as Sta, isoleucine as Ile and norleucine as Nle. The aminoprotecting group t-butoxycarbonyl is abbreviated as Boc, benzyloxycarbonyl as CBZ and N-t-butoxycarbonyl on the imidazole of histidine as imBoc. Further, the substituent $R_2$ is inter alia of the formula

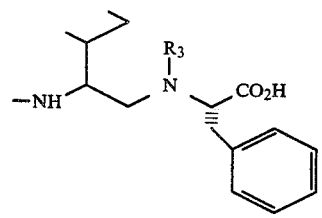

and is abbreviated as IleRPhe. When $R_3$ is other than hydrogen it is abbreviated as IleR($R_3$)Phe.

The modified cyclostatine containing an additional oxygen or nitrogen in the structure are of the formula

wherein X is oxygen, amino or a substituted amino as previously defined. These structures are abbreviated as 2-oxahomocyclohexylSta and 2-azahomocyclohexylSta.

All the natural amino acid contained in the structures of the instantly claimed compounds are of the L configuration, the naturally occurring configuration, unless otherwise noted.

DETAILED DESCRIPTION OF THE INVENTION

The compounds of this invention exhibit antihypertensive activity in vivo in mammals, including humans. At least a substantial portion of this activity results from their ability to inhibit the cleavage of angiotensinogen by renin. Although we do not wish to be limited by the following theory of mechanism, it is likely that the mechanism of the renin-inhibiting activity of the compounds of the invention is their selective binding (as compared to angiotensinogen) to renin. The compounds of the invention exhibit an enzyme-inhibiting activity that is selective for renin as against other beneficial enzymes such as cathepsin D. Because of their low molecular weights they exhibit favorable solubility characteristics in aqueous media, thus making oral administration feasible, and can be synthesized at a commercially realistic cost. The compounds of the present invention are also useful against congestive heart failure.

The compounds of the invention may be prepared by methods familiar to those skilled in the art. The basic sub-unit of the preferred chemical synthesis is the acylation of the unprotected alpha-amino group of an amino acid residue with an amino acid having an activated (for acylation purposes) carboxylic function and a suitable protecting group bonded to its own alpha-nitrogen to form a peptide bond between the two amino acid residues, followed by the removal of said protecting group. This synthesis sub-unit of couplingdeblocking is performed repeatedly to build up the polypeptide, starting from the C-terminal end of the molecular structure and working to the N-terminal end as described herein. The amino acids (including statine) utilized to synthesize the compounds of the present invention are commercially available (as free acids, salts or esters, etc.) in both alpha-amino protected and alpha-amino unprotected forms.

Synthesis of the intermediate forming the skeleton of 2-oxahomocyclohexylstatine having the structure

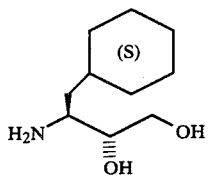

starts with reduction of N-BocPhe methyl ester to the corresponding aldehyde using diisobutylaluminum hydride. The resulting aldehyde is subsequently treated with potassium cyanide providing the appropriate cyanohydrin, containing the desired stereochemistry as follows:

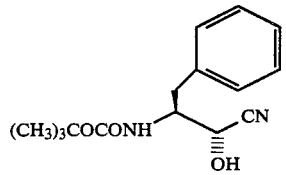

The resulting cyanohydrin is hydrolyzed step-wise, via its o-t-butyldimethylsilyl derivative, to the corresponding amide and then acid. The phenyl group of the resulting acid is reduced with rhodium and hydrogen to cyclohexyl and the acid converted to the methyl ester. Reduction of the ester moiety, the hydroxy group having been transformed to a benzyloxy, provides the following intermediate:

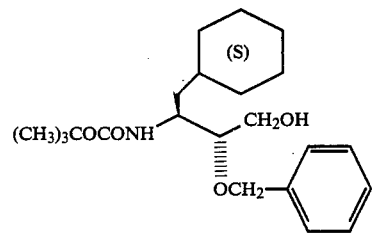

Synthesis of the intermediate forming the skeleton of 2-azahomocyclohexylstatine having the structure

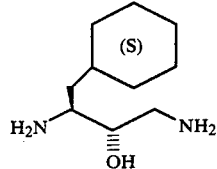

starts with the reduction of the previously described cyanohydrin, having the hydroxy group protected with a t-butyldimethylsilyl group, with 5% rhodium on carbon to give the corresponding amine. The amine, acylated with trifluoroacetic anhydride, is subjected to reduction using 10% rhodium on carbon. The N-trifluoroacetyl group of the resulting cyclohexyl product is removed with ethanol-sodium borohydride to provide the following intermediate:

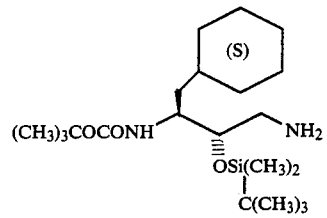

Further alkylation of the free amino moiety can be affected by reductive alkylation using an aldehyde or ketone and sodium cyanoborohydride.

The reduced form of isoleucylphenylalanine of the structure

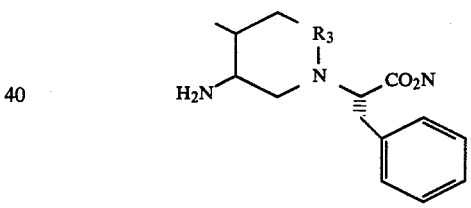

is prepared by reducing N-t-butoxycarbonyl-L-isoleucine methyl ester to the corresponding aldehyde using diisobutyl aluminum hydride. The resulting aldehyde is condensed with phenylalanine benzyl ester under reductive alkylating conditions to give the desired intermediate as the N-t-butoxycarbonyl benzyl ester derivative.

Reductive alkylation is employed for the synthesis of IleR($R_3$)Phe wherein $R_3$ is —$(CH_2)_5CN$, using 5-formylvaleronitrile and BocIleRPhe benzyl ester and sodium cyanoborohydride as the reducing agent.

Reduction of the final peptide containing —IleR$(CH_2)_5$CN)Phe— is employed to synthesize those polypeptides where $R_3$ is omega-aminohexyl, $(CH_2)_6NH_2$.

The activity of the compounds of the present invention as inhibitors of the angiotensinogen-cleaving activity of renin may be determined by studying (1) their ability to inhibit the angiotensinogen-cleaving activity of renin in vitro and (2) their ability to antagonize the exogenous renin-induced pressor response in vivo.

The compounds of the present invention can be administered as antihypertensive agents by either the oral or parental routes of administration, with the former being preferred for reasons of patient convenience and comfort. In general, these antihypertensive compounds are normally administered orally in dosages ranging from about 0.5 mg. to about 50 mg. per kg. of body weight per day and 0.1 mg. to about 5 mg. per kg. of body weight per day when given parenterally; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

The novel compounds of the invention can be orally administered in a wide variety of different dosage forms, i.e., they may be formulated with various pharmaceutically-acceptable inert carriers in the form of tablets, capsules, lozenges, troches, hard candies, powders, sprays, aqueous suspensions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired of oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The following examples illustrate the invention but are not to be construed as limiting the same.

EXAMPLE 1

BocPheHis-2-oxahomocyclohexylStaLysPhe Methyl Ester ($R_1=H$; $R_2=$LysPhe; and $X=O$)

A.
N-t-Butoxycarbonyl-(S)-3-amino-(R)-2-hydroxy-4-phenylbutyronitrile

N-t-Butoxycarbonyl-L-phenylalanine methyl ester (250 g., 0.90 mol) was dried by addition and removal at reduced pressure of 1.0 l. dry toluene, and dissolved in dry toluene (3 l.) in a 12 l. flask equipped with septum, nitrogen inlet, overhead stirrer, and thermometer. The solution was cooled to $-78°$ C. and a solution of diisobutylaluminum hydride was added via cannula over a period of 0.5 hour so that the temperature was maintained below $-70°$ C. After being stirred an additional 15 minutes, absolute methanol (250 ml.) was added (dropwise at first until vigorous effervescence subsided) at $-78°$ C. followed 20 minutes later by 3.0 l. of 50% Rochelle salt solution (also slowly at first). Diethyl ether (2 l.) was added to the mixture, and the temperature was raised to 20° C. On standing the layers separated, and the aqueous was extracted with ether ($2 \times 1.5$ l.). The organic phase was washed with brine, dried sodium sulfate and concentrated to give crude N-t-butoxycarbonyl-L-phenylalaninal which was used immediately without purification.

The crude aldehyde was dissolved in 1.5 l. dimethoxyethane, and treated slowly with an ice-cold solution of sodium bisulfite (105 g., 1.0 mol) in water (1.5 l.) so that the temperature did not exceed 10° C. After being stirred at 14° C. for 10 hours and at 25° C. for 6 hours, the solution was concentrated at reduced pressure to a volume of 1.0 l., mixed with 3.5 l. ethyl acetate, and at 21° C. a solution of potassium cyanide (65 g., 1.0 mol) in water (300 ml.) was added over 5 minutes, and the mixture was stirred at 25° C. for 16 hours. The layers were separated, and the aqueous extracted with ethyl acetate. The organic layers were washed with brine, dried over sodium sulfate and concentrated to an oil which was dissolved in 375 ml. ethyl ether. To this solution was added 1 l. hexane. Crystallization began in a few minutes, and the chilled mass was filtered and washed with 800 ml. 1:3 ether-hexane. The dried material (49%, 122 g.) was contaminated with 18% of the 2-(S) epimer, determined by RP-HPLC as described below. The material was twice recrystallized in the manner described above to give 60.9 g., 25% overall, of stereoisomerically pure hydroxynitrile mp 115°–116° C. (uncorrected). Less than 1% of the 2-(S) isomer was present by HPLC, and the substance eluted in 8.2 minutes on a Dupont Zorbax C-8 reverse-phase $250\times4.6$ mm column in 40/60 acetonitrile-water at 1.5 ml./min., 214 nm detection.

NMR (250 mHz, CDCl$_3$): delta 1.40 (s, 9H, Boc), 2.90 and 3.14 (dd, 1H ea, ArCH$_2$), 4.00 (m, 1H, NCH), 4.58 (m, 1H, CHCN), 5.14 (m, 2H, NH and OH) ppm.

[alpha]$_D^{22}$ $-58.1°$, (C=1.145, CHCl$_3$).

B.
N-t-Butoxycarbonyl-(S)-3-amino-(R)-2-t-butyldimethylsilyloxy-4-phenylbutyronitrile A solution of N-t-butoxycarbonyl-(S)-3-amino-(R)-2-hydroxy-4-phenylbutyronitrile (15.2 g., 55.0 mmol) and imidazole (2.5 equiv., 9.35 g.) in anhydrous dimethylformamide (125 m.) was cooled to 0° C., treated with t-butyldimethylchlorosilane (77.0 mmol, 11.6 g.), and brought to 25° C. After 3.5 hours, the solution was concentrated in vacuo and dissolved in ethyl acetate (300 ml.). The mixture was washed twice with small portions of aqueous 1M lithium chloride, with aqueous 1N HCl ($2\times 100$ ml.), brine, and dried over magnesium sulfate. The oil obtained on after evaporation of solvent was chromatographed on silica (600 g. of 0.06-0.2 mm eluting sequentially with 1:25 ethyl acetate-hexanes (2 l.), 1:15 ethyl acetate-hexanes, and 1:7 ethyl acetate-hexanes. The silyl ether obtained on solvent removal was a colorless syrup (21.5 g., 100%).

[alpha]$_D^{22}$ $-32.1°$, (C=1.09, CHCl$_3$).

NMR (CDCl₃, 60 mHz), partial: delta 0.03, 0.06 (s, 3H, Si(Me)2), 0.8 (s, 9H, Si(t-Bu), 1.2 (s, 9H, t-BuO), 2.75–2.95 (m, 2H, CH₂), 3.6–4.1 (m, 1H, —CHCN), 4.5 (br, 1H, NH), 7.05 (s, 5H, Ph) ppm.

C.
N-t-Butoxycarbonyl-(S)-3-amino-(R)-2-t-butyldimethylsilyloxy-4-phenylbutyramide A solution of N-t-butoxycarbonyl-(S)-3-amino-(R)-2-t-butyldimethylsilyloxy-4-phenylbutyronitrile (22.7 g., 58.0 mmol) in absolute ethanol (500 ml) was chilled in an ice bath and treated in one portion with aqueous 1N sodium hydroxide (100 ml.). Dropwise addition of aqueous 30% H₂O₂ (200 ml.) was commenced with simultaneous cooling and stirring so that a temperature of less than 6° C. was maintained during this addition. After 2 hours at 3° C. the mixture was treated with 100 ml. of aqueous 20% sodium thiosulfate with cooling (reaction temperature maintained below 0° C. with a dry ice-acetone bath). The mixture was concentrated to remove most of the ethanol, extracted with ethyl acetate (3×200 ml.), which was washed with brine and dried over magnesium sulfate. Chromatography on silica (0.04–0.06 mm.), elution performed with ethyl acetate-hexane (1:3, 1 l.; then 1:2) gave after solvent removal in vacuo 14.3 g., (60.5%) of the silyl amide as a colorless waxy solid.

NMR (250 mHz, CDCl₃), partial: delta 0.0, 0.03 (s, 3H, SiMe₂), 0.8 (s, 9H, t-BuSi), 1.13 and 0.97 (s, 9H total, Boc), 2.3–2.4 and 2.8–2.9 (m, 1H ea, PhCH), 4.1–3.9 (m, 2H, NCHCHCON), 4.9 and 5.15 (d, 1H total, J=10Hz, Boc NH), 7.1–7.2 (m, 5H, Ph) ppm. The compound is present in two rotameric forms as evidenced by the doubled Boc and BocNH resonances.

D. (S)-3-amino-(R)-2-hydroxy-4-phenylbutyramide hydrochoride

N-t-Butoxycarbonyl-(S)-3-amino-(R)-2-t-butyldimethylsilyloxy-4-phenylbutyramide (14.2 g., 34.8 mmol) was placed in a dry flask under nitrogen and dissolved in cold (0° C.) anhydrous 4N hydrogen chloride/1,4-dioxane. The solution was brought to 25° C., and the suspension which quickly developed was stirred for 2 hours. The mixture was concentrated at reduced pressure, and the residual solid was suspended in ether (250 ml.) and filtered. The colorless solid was washed with ether and dried, giving 7.53 g. (94%) of the above titled hydrochloride. A sample recrystallized from 90/10 ethanol-water showed mp 264°–265° C. (uncorr.) and [alpha]$_D^{22}$ −1.3°, (c=0.7, H2O).

NMR (250 mHz, D₂O), partial: delta 3.05–3.26 (two AB quartets, 2H total, PhCH₂), 3.97 (dt, 1H, J=3Hz, 8Hz, NCH), 4.30 (d, 1H, J=3Hz, CH—O), 7.3–7.6 (m, 5H, Ph) ppm.

E. (S)-3-amino-(R)-2-hydroxy-4-phenylbutyric acid (S)-3-amino-(R)-2-hydroxy-4-phenylbutyramide hydrochloride (7.43 g., 32.2 mmol) was dissolved in 6N hydrochloric acid (160 ml.), warmed to 50° C., and brought from 50° C. to 85° C. over 30 minutes. The resulting solution was kept at 85° C. for 35 minutes, filtered through Celite, and concentrated to give a wet solid. The solid was dissolved in water (30 ml.) and the solution was adjusted to pH 6.0. The precipitate was collected by filtration at 0° C. and washed with cold water (2×10 ml.), and dried in vacuo at 110° C. to give the title acid,

[alpha]$_{578}$= −28.2° (c=1.32, 1N HCl).

Lit: J. Med. Chem. (1977) 20, 510, [alpha]$_{578}$ −31°, (concentration unspecified, 1N HCl).

F.
(S)-3-t-butoxycarbonylamino-(R)-2-hydroxy-4-phenylbutyric acid (S)-3-amino-(R)-2-hydroxy-4-phenylbutyric acid (5.2 g., 26.6 mmol) was dissolved in dioxane-water (2.5:1, respectively, 70 ml.) at 25° C. and the pH was adjusted to 12.0 with 6N sodium hydroxide. Di-t-butyldicarbonate (1.5 equiv., 8.8 ml.) was added, and the mixture was stirred and treated with additional 6N sodium hydroxide as required to keep the pH above 11. Two additional lots of di-t-butyl dicarbonate were added (4 ml. each) together with addition sodium hydroxide solution to keep the pH above 11, until HPLC indicated over 90% conversion of the starting amino acid. The mixture was brought to pH 11, concentrated to remove most of the dioxane, and extracted twice with ether. The aqueous portion was then stirred with ethyl acetate (200 ml.) at 0° C., whilst the pH was brought to 1.5 by addition of 6N hydrochloric acid. The layers were separated, and the aqueous layer was extracted with ethyl acetate. The organic layers were combined, washed with brine, and dried over magnesium sulfate. Solvent evaporation gave 7.45 g. of a yellowish foam (94%) which was used without further purification.

[alpha]$_D^{22}$ −55.1 (c=1.18, CHCl₃)

NMR (250 mHz, CDCl₃), partial: delta 1.37 (s, 9H, Boc); 2.9–3.0 (m, 2H, CH₂), 4.0–4.25 (m, 2H, CH—CH); 5.0 (br, 1H); 7.5 (br, 1H), 7.2–7.4 (m, 5H, Ph) ppm.

G.
(S)-3-t-butoxycarbonylamino-(R)-2-hydroxy-4-cyclohexylbutyric acid (S)-3-t-butoxycarbonylamino-(R)-2-hydroxy-4-phenylbutyric acid (7.28 g., 24.7 mmol) was dissolved in 150 ml. absolute methanol and 20 ml. glacial acid and shaken with 1.66 g. of 10% Rhodium on carbon (Engelhard Corp.) for 5 hours under a 52 p.s.i. hydrogen atmosphere. The mixture was then filtered, concentrated, and coevaporated with toluene three times, and dried at high vacuum. The oil obtained (7.15 g., 96%), was used without purification.

NMR (250 mHz, CDCl₃), partial: delta, 0.9–1.8 (m, cyclohexyl), 1.43 (s, 9H, Boc), 4.0–4.2 (m, 2H, CH—CH), 4.9 (br, 1H), 6.1 (br, 1H) ppm.

[alpha]$_D^{25}$ −40.7° (c=1.08, CHCl₃).

H.
(S)-3-t-butoxycarbonylamino-(R)-2-hydroxy-4-cyclohexylbutyric acid methyl ester (S)-3-t-butoxycarbonylamino-(R)-2-hydroxy-4-cyclohexylbutyric acid (6.09 g., 20.2 mmol) was dissolved in ether (30 ml.) and treated at 0° C. dropwise with a solution of diazomethane in ether (c.a. 0.3M, from N'nitroso-N-methyl-N-nitroguanidine and NaOH) until the yellow color of excess diazomethane persisted. The excess diazomethane was decomposed by addition of several drops of acetic acid, and the mixture was concentrated, and chromatographed on 250 g. silica (0.04–0.06 mm), eluting with ethyl acetate-hexanes (500 ml. of 1:8, 1.4 l. of 1:6, then 1:4). The methyl ester was obtained as a solid on solvent removal (5.33 g., 84%). A portion recrystallized from hexane melted at 69–70° C. and showed

[alpha]$_D^{25}$ −71.1° (c=0.675, CHCl₃).

The major portion was used without purification and showed

[alpha]$_D^{25}$ −71.8° (c=1.08, CHCl$_3$).

NMR (250 mHz, CDCl$_3$): delta, 0.8–2.9 (m, C$_6$H$_{13}$CH$_2$), 1.42 (s, 9H, Boc), 3.08 (d, 1H, J=6Hz, OH), 3.80 (s, 3H, OCH$_3$), 4.1–4.15 (m, 2H, CH—CH), 4.60 (d, 1H, J=9Hz, BocNH) ppm.

I. (S)-3-t-butoxycarbonylamino-(R)-2-benzyloxy-4-cyclohexylbutyric acid methyl ester (S)-3-t-butoxycarbonylamino-(R)-2-hydroxy-4-cyclohexylbutyric acid methyl ester (4.58 g., 14.52 mmol) was dissolved in anhydrous dimethylformamide (30 ml.) together with benzyl bromide (2.6 ml., 21.7 mmol) and cooled to 0° C. Sodium hydride (freed of oil by washing with hexane, 450 mg., 19.6 mmol) was added in one portion and the mixture was stirred under nitrogen and allowed to warm to 25° C. over a period of about 15 minutes. The mixture was poured slowly into a stirred ice-cooled mixture of ether (500 ml.) and excess aqueous 1N hydrochloric acid, and was then combined with two previous reaction mixtures where a total of 4.27 mmol (1.34 g.) of this hydroxy methyl ester had been etherified and worked up in an identical fashion. The ether layer was separated and the aqueous layer was extracted thoroughly with ether. The ether layers were combined and washed with 1M lithium chloride solution (2×30 ml.), and dried over magnesium sulfate. The concentrate was chromatographed on silica (0.032–0.064 mm) in 1:6 ether-hexane. Several impure fractions were combined, concentrated, and re-chromatographed on 50 g. silica, eluting with 1:10 ether-hexane. The pure fractions combined and concentrated gave 6.45 g. (85%) of the benzyl ether.

[alpha]$_D^{25}$ −6.8° (c=1.175, CHCl$_3$).

NMR (250 mHz, CDCl$_3$): delta 1.40 (s, 9H, Boc); 0.8–1.8 (m, C$_6$H$_{13}$CH$_2$), 3.83 (s, 3H, OCH$_3$), 3.9 (d, 1H, J=2Hz, BnOCH—), 4.17 (dt, 1H, NCH), 4.37 (d, 1H, J=12Hz, PhCH), 4.80 (d, 1H, J=12Hz, PhCH), 7.34 (s, 5H, Ph) ppm.

J. (S)-3-t-butoxycarbonylamino-(R)-2-benzyloxy-4-cyclohexyl-1-butanol (S)-3-t-butoxycarbonylamino-(R)-2-benzyloxy-4-cyclohexylbutyric acid methyl ester (1.80 g., 4.44 mmol) was dissolved in a mixture of tetrahydrofuran (6 ml.), ethanol (6 ml.), and water (0.05 ml.) and treated with a total of 510 mg. sodium borohydride (13.4 mmol) and 875 mg. lithium chloride (20 mmol) and stirred 20 hours at 25° C. The mixture was poured into 200 ml. ether and 25 ml. water, and the stirring mixture was chilled at 0° C. whilst treated dropwise with 6N hydrochloric acid until the pH of the aqueous phase was 1.0. The organic layer was separated, and the aqueous layer was saturated with sodium chloride and extracted several times with ether. The organic layers were washed with aqueous 10% sodium bicarbonate and dried over magnesium sulfate. Concentration gave 1.64 g. of the protected aminodiol as a colorless solid, showing

[alpha]$_D^{25}$ −47.8 (c=1.15, CHCl$_3$).

This material was used without purification. A sample recrystallized from hexane gave mp=103°–106° C.,

[alpha]$_D^{25}$ −49.6 (c=0.675, CHCl$_3$).

and the following data.

NMR (250 mHz, CDCl$_3$): delta 0.8–1.8 (m, C$_6$H$_{13}$CH$_2$), 1.43 (s, 9H, Boc), 3.4–3.5 (m, 2H, CH$_2$OH), 3.6 (br, 1H, OH), 3.73 (m, 1H, BnOCH), 4.0 (dt, 1H, NCH), 4.54 and 4.62 (d, each 1H, OCH$_2$Ph), 4.6 (d, 1H, BocNH), 7.3–7.4 (m, 5H, Ph) ppm.

K. N-t-Boc-O-benzyl-2-oxahomocyclohexylStaLys-(e-CBZ)Phe benzyl ester

A solution of (S)-3-t-butoxycarbonylamino-(R)-2-benzyloxy-4-cyclohexyl-1-butanol (0.250 g., 0.663 mmol) and 2,6-lutidine (0.085 ml.) in dry toluene (2.5 ml.) was added dropwise to a stirred solution of phosgene (200 mg., 2.0 mmol) in toluene (1.2 ml.) at 0° C. over a several minute period, and the resulting solution was brought to 25° C. After 15 minutes this solution was added dropwise to at 0° C. solution of e-carbobenzyloxylysylphenylalanine benzyl ester hydrochloride (440 mg., 0.795 mmol) and 2,6-lutidine (0.20 ml.) in 6 ml. dichloromethane, and the resulting mixture was warmed to 25° C. over 10 minutes. This reaction mixture was combined with another mixture derived in an identical fashion from 100 mg. (0.265 mmol) of the starting protected aminodiol, and the resulting dichloromethane solution was washed twice with excess 1N hydrochloric acid, with 1N sodium hydroxide, dried over magnesium sulfate, and concentrated. Chromatography on 20 g. silica (0.04–0.06 mm) in 1:2 ethyl acetate-hexane followed by 1:1 ethyl acetate-hexane gave 740 mg. (87%) of the title carbamate as a colorless amorphous foam.

NMR (250 mHz, CDCl$_3$), partial: delta, 1.41 (s, 9H, Boc), 3.1–3.2 (m), 3.6 (m, 1H,), 3.9 (m, 1H), 4.05–4.25 (m), 4.52 and 4.70 (d, J=12Hz, 1H ea, BnoCH$_2$), 4.89 (dt, J=8Hz, 1H), 5.0–5.35 (m), 7.0 (m, 2H), 7.2–7.5 (m, aromatic) ppm.

L. O-benzyl-2-oxahomocyclohexylStaLys(e-CBZ)Phe benzyl ester hydrochloride

N-t-Boc-O-benzyl-2-oxahomocyclohexylStaLys(e-CBZ)-Phe Benzyl ester (905 mg., 0.983 mmol) was dissolved in 8 ml. of 4N hydrochloric acid dioxane at 0° C., and the mixture was stirred 6 hours at 25° C. The mixture was concentrated at reduced pressure and co-evaporated twice with ether to give after drying in vacuo at 56° C. 790 mg. (96%) of the colorless hydrochloride.

NMR (DMSO, 250 mHz), partial: delta, 0.7–1.7 (m), 2.9–3.1 (m, 2H, phenylalaninyl CH$_2$), 4.56 and 4.72 (d, 1H ea, J=12Hz, benzyl ether CH$_2$), 5.02 and 5.06 (s, 2H ea, CBZ and benzyl ester CH$_2$), 7.2–7.5 (m, aromatic), 7.50 and 8.50 (d, 1H ea, NH) ppm.

M. BocPheHis(imBoc)-O-benzyl-2-oxahomocyclohexylStaLys(e-CBZ)Phe benzyl ester O-Benzyl-2-oxahomocyclohexylStaLys(e-CBZ)Phe benzyl ester hydrochloride (750 mg., 0.891 mmol), triethylamine (0.136 ml.), 1-hydroxybenzotriazole hydrate (286 mg.) and Bis-(N,im)-t-butoxycarbonyl-L-phenylalanyl-L-histidine (540 mg., 1.11 mmol) were dissolved in dichloromethane at 0° C. and treated with dicyclohexylcarbodiimide (228 mg., 1.11 mmol). Stirring was continued at 0° C. for 1.5 hours and for 4.5 hours more at 25° C. The mixture was filtered, concentrated, dissolved in ethyl acetate (25 ml.) and after being stirred 10 minutes filtered again, and the filtrate was washed with 1N sodium hydroxide (2×5 ml.), dried over magnesium sulfate and concentrated. The foam obtained was chromatographed on 85 g. silica (0.04–0.06 mm) eluting with ethanol in methylene chloride 300 ml. each of 0.3%, 0.8%, 2%, 3% and 4%, and the compound was isolated after concentrated in 69% yield (800 mg.) as an amorphous foam.

NMR (250 mHz, CD$_3$OD), partial: delta 1.35 and 1.59 (s, 9H, ea, Boc and imBoc), 4.52 and 4.68 (d, 1H ea, J=12Hz, benzyl ether CH$_2$), 5.05 and 5.09 (s, 2H ea, CBZ and benzyl ester CH$_2$O), 7.1–7.4 (m, aromatic), 8.07 (s, 1H, imidazolyl H$_2$) ppm.

N. BocPheHis-2-oxahomocyclohexylStaLysPhe methyl ester

BocPheHis(imBoc)-O-benzyl-2-oxahomocyclohexyl-StaLys(e-CBZ)Phe benzyl ester (780 mg., 0.598 mmol) in anhydrous methanol (5 ml.) was treated at 25° C. with anhydrous potassium carbonate (0.05 equiv) for 45 minutes, at which time TLC (silica, 5% methanol in dichloromethane) indicated complete conversion to a more polar substance. The solution was diluted with 20 ml. methanol and 4 ml. gl acial acetic acid, and 100 mg. of 20% Pd(OH)$_2$/C (Pearlman's catalyst, Aldrich Chemical Co.) was added. The mixture was shaken under 50 p.s.i. hydrogen for 6 hours, filtered through Celite, and concentrated to give 640 mg. (95%) of the intermediate O-benzyl methyl ester acetate salt as determined by 250 mHz NMR. This material was redissolved in 10 ml. 1:1 methanol-acetic acid and shaken with 180 mg. 10% Pd/C (fa Corp.) for 24 hours under 50 p.s.i. hydrogen, filtered through Celite, and concentrated to give after drying at 56° C. in vacuo a beige amorphous powder (450 mg., 83%) whose spectral and chromatographic properties were consistent with those expected of the title methyl ester.

NMR (250 mHz, CD$_3$OD), partial: delta 1.35 (s, 9H, Boc), 3.70 (s, 3H, OCH$_3$), 6.93 (s, 1H, imidazolyl H$_5$), 7.67 (s, 1H, imidazolyl H$_2$), 7.1–7.3 (m, aromatic) ppm.

EXAMPLE 2

BocPheHis-2-N-i-propylazahomocyclohexylStaLys-Phe (R$_1$=H; R$_2$=LysPhe; and X=NCH(CH$_3$)$_2$)

A.
3-(S)-N-t-Butoxycarbonylamino-(R)-t-butyldimethylsilyloxy-4-phenyl-1-butylamine N-t-Butoxycarbonyl-(S)-3-amino-(R)-2-t-butyldimethylsilyloxy-4-phenylbutyronitrile (5.0 g., 12.8 mmol) was dissolved in absolute ethanol (100 ml.) and cooled in an ice bath whilst anhydrous ammonia (2 g.) was introduced. 5% Rhodium on carbon (Aldrich) was added, and the mixture was shaken under 50 p.s.i. hydrogen for 18 hours. Filtration through Celite and concentration at reduced pressure gave the primary amine as a colorless oil which was used without purification in subsequent steps. Yield, 4.90 g. (97%).

NMR (CDCl$_3$, 250 mHz): delta 0.10 and 0.13 (s, 3H, ea, SiMe2), 0.95 (s, 9H, t-BuSi), 1.35 (s, 9H, Boc), 1.92 (br, 2H, NH$_2$), 2.65–2.85 (m, 4H, NCH$_2$ and PhCH$_2$), 4.12 and 3.71 (m, 1H ea, NCHCHO), 4.67 (d, 1H, J=10Hz, BocNH), 7.2–7.45 (m, 5H, aromatic) ppm.

B.
N-[3(S)-N-t-Butoxycarbonylamino-2(R)-t-butyldimethylsilyloxy-4-phenyl-but-1-yl]trifluoroacetamide 3(S)-N-t-Butoxycarbonylamino-2(R)-t-butyldimethylsilyloxy-4-phenyl-1-butylamine (9.75 g., 24.7 mmol) and diisopropylethylamine (6.45 ml., 37.1 mmol) in dichloromethane (50 ml.) was cooled to 0° C. and treated with trifluoroacetic anhydride (4.2 ml., 29.6 mmol) over a period of 5 minutes. Another 1.0 ml. (7.0 mmol) of the anhydride was then added dropwise, and the mixture was diluted with dichloromethane (100 ml.), washed with water (2×50 ml.), ice-cold 1N HCl (3×50 ml.), water (3×50 ml.), dried over magnesium sulfate, and concentrated at reduced pressure to give the trifluoroacetamide as a pale yellow oil which was used without purification in subsequent steps. Yield, 10.61 g., 88%.

NMR (CDCL$_3$, 250 mHz): delta, 0.14 and 0.18 (s, 3H ea, SiMe2), 0.96 (s, 9H, t-BuSi), 1.36 (s, 9H, Boc), 2.7–2.9 (m, 3H, PhCH$_2$ and SiOCH), 3.8 (m, 2H, NCH$_2$), 3.97 (m, 1H, NCH), 4.6 (d, 1H, J=10H, BocNH), 7.1–7.4 (m, 5H, aromatic), 7.9 (br, 1H, CF$_3$CONH) ppm.

C.
N-[3(S)-N-t-Butoxycarbonylamino-2(R)-t-butyldimethylsilyloxy-4-cyclohexyl-but-1-yl]trifluoroacetamide N-[3(S)-N-t-Butoxycarbonylamino-2(R)-t-butyldimethylsilyloxy-4-phenyl-but-1-yl]trifluoroacetamide (10.6 g., 21.5 mmol) was dissolved in methanol (150 ml.) and shaken with 10% Rhodium on carbon 1.0 g., Engelhard Corp. under 50 p.s.i. for 24 hours at 25° C. The mixture was filtered through Celite and concentrated in vacuo to give 10.91 g. (100%) of a colorless foam which was chromatographed on 400 g. silica (0.04–0.06 mm) in ethyl acetate-hexane (1:20) to give after solvent evaporation 8.50 g. (79%) of the title amide as a colorless oil.

NMR (250 mHz, CDCl$_3$), partial: delta 0.9 (s, 9H, tBuSi), 1.47 (s, 9H, Boc), 2.76 (m, 1H, SiOCH), 3.6–3.85 (m, 3H, NCH and NCH$_2$), 4.49 (d, 1H, J=10 Hz, BocNH), 8.0 (br, 1H, NHCOCF$_3$) ppm.

D.
3(S)-N-t-Butoxycarbonylamino-2(R)-t-butyldimethlysilyloxy-4-cyclohexyl-1-butylamine N-[3(S)-N-t-Butoxycarbonylamino-(R)-t-butyldimethylsilyloxy-4-cyclohexyl-but-1-yl]trifluoroacetamide (6.98 g., 14.1 mmol) was dissolved in absolute ethanol and chilled in an ice bath while sodium borohydride (2.13 g., 56.4 mmol) was added. The mixture was then stirred for 2 hours at 25° C. and at 0° C. for 12 hours. The mixture was concentrated, taken up in ether (200 ml.), washed with water (3×25 ml.). The aqueous washes were extracted once with ether, and the combined organic layers were combined, dried over magnesium sulfate, and concentrated to give in quantitative yield the amine as a colorless oil which was used without further purification, weight 6.00 g.

NMR (250 mHz, CDCL$_3$), partial: delta 0.1 (s, 6H, SiMe2), 0.89 (s, 9H, t-BuSi), 1.42 (s, 9H, Boc), 2.64 (d, 2H, J=7 Hz, NCH$_2$), 3.53 (m, 1H, OSiCH), 3.9 (m, 1H, NCH), 4.5 (d, 1H, J=10 Hz, BocNH) ppm.

E.
N-isopropyl-(S)-N-t-butoxycarbonylamino-2(R)-t-methylsilyloxy-4-cyclohexyl-1-butylamine 3(S)-N-t-Butoxycarbonylamino-2(R)-t-butyldimethylsilyloxy-4-cyclohexyl-1-butylamine (0.959 g., 2.39 mmol) was dissolved in methanol (10 ml.) and treated sequentially with glacial acetic acid (0.68 ml.), 600 mesh 3 angstrom molecular sieves (Alfa, 1 g.), sodium cyanoborohydride (0.15 g., 2.39 mmol), and finally at 25° C. dropwise over 2–3 minutes with acetone (0.175 ml., 2.39 mmol). After 1 hour, another 0.05 ml. acetone was added and stirring was continued another 60 minutes, the mixture was filtered through Celite, concentrated, dissolved in ethyl acetate, and was filtered through Celite, concentrated, dissolved in ethyl acetate, and washed with 10% sodium bicarbonate solution. The aqueous phase was adjusted with sodium hydroxide to pH 10 and was re-extracted once with ethyl acetate. The combined organic layers were washed with aqueous 10% bicarbonate and water, dried over sodium sulfate, and concentrated at reduced pressure to give 0.970 g. (93%) of the title amine as a colorless oil which was not further purified.

NMR (90 mHz, CDCL$_3$), partial: delta, 0.89 (s, 9H, t-BuSi), 1.04 (d, 6H, J=6 Hz, C(CH$_3$)$_2$), 1.42 (s, 9H, Boc), 2.55 (d, 2H, NCH$_2$), 2.75 (septet, 1H, NCH(Me), 3.6–4.0 (m, 2H, NCHCHO), 4.60 (d, 1H, J=10 Hz, BocNH) ppm.

F.
N-t-Butoxycarbonyl-O-t-butyldimethylsilyl-2-N-i-propylazahomocyclohexylStaLys(e-CBZ)Phe benzyl ester A solution of e-carbobenzyloxy-L-lysylphenylalanine benzyl ester (1.41 g., 2.55 mmol) and triethylamine (0.354 ml., 2.55 mmol) in dichloromethane (2.0 ml.) was added dropwise at 0° C. to a solution of imidazole (0.174 g., 2.55 mmol) and N,N'-carbonyldiimidazole (0.487 g., 3.00 mmol) and stirring was continued for 50 minutes at that temperature. 1-N-isopropyl-3(S)-N-t-Butoxycarbonylamino-2(R)-t-butyldimethylsilyloxy-4-cyclohexyl-1-butylamine (0.454 g., 1.13 mmol) in dichloromethane (2.0 ml.) was added and the mixture was allowed to warm to 25° C. and was stirred there for 46 hours. The mixture was diluted with dichloromethane and washed twice with 1N HCl (3 ml. ea.), water (2×2 ml.), dried over magnesium sulfate and concentrated. Chromatography on 120 g. silica, eluting with ethyl acetate-hexane (a gradient from 30% to 40%) gave the protected urea as a colorless foam (1.07 g., 56%).

NMR (90 mHz, CDCl$_3$), partial: delta 0.87 (s, 9H, t-BuSi), 1.15 (d, 6H, J=7 Hz, NCH(Me)), 1.42 (s, 9H, Boc), 5.1 (m, CBZ and benzyl ester CH$_2$), 6.9–7.4 (m, aromatic) ppm.

G. 2-N-i-PropylazahomocyclohexylStaLys(e-CBZ)Phe benzyl ester hydrochloride

N-t-Butoxycarbonyl-O-t-butyldimethylsilyl-2-N-isopropylazahomoC-StaLys(e-CBZ)Phe benzyl ester (1.01 g., 1.03 mmol) was dissolved in acetonitrile (24 ml.) and treated at 25° C. with 1.25 ml. of aqueous 48% hydrofluoric acid after being stirred for 20 minutes, the reaction mixture was treated with excess solid sodium bicarbonate and concentrated at reduced pressure. Ethyl acetate was added, and the mixture was washed with water, dried over magnesium sulfate, and concentrated to give a colorless foam, weight 0.936 g. To this was added 20 ml. of 4N anhydrous hydrogen chloride-dioxane, and after being stirred 20 minutes at 25° C., the mixture was concentrated, coevaporated with several portions of ether, and dried in vacuo, giving 0.855 g., (quantitative) of an amorphous beige foam.

NMR (250 mHz, DMSO-D6), partial: delta 1.08 (d, 6H, J=5 Hz, (Me)$_2$CH), 5.0–5.2 (m, CBZ and benzyl ester CH$_2$), 7.4–8.0 (aromatic) ppm.

H.
BocPhe(N-imBoc)His-2-N-isopropylazahomocyclohexylStahys(e-CBZ)Phe benzyl ester 2-N-i-PropylazahomocyclohexylStaLys(e-CBZ)Phe benzyl ester hydrochloride (0.410 g., 0.507 mmol) was dissolved in dichloromethane (1.5 ml.), and treated at 0° C. sequentially with triethylamine (0.092 ml., 0.659 mmol), N-t-butoxycarbonyl-L-phenylalaninyl(N-im-t-butoxycarbonyl)-L-histidine (0.280 g., 0.558 mmol), 1-hydroxybenzotriazole hydrate (0.132 g., 0.862 mmol), and dicyclohexylcarbodiimide (0.115 g., 0.558 mmol), and the mixture was stirred 4 hours at 0° C. and 20 hours at 25° C. The mixture was filtered concentrated, dissolved in ethyl acetate, filtered, washed with 1N sodium hydroxide (2×1 ml.), brine (1 ml.) dried over magnesium sulfate and concentrated. The foam obtained (0.654 g.) was chromatographed on 35 g. silica (0.04–0.06 mm) eluting with ethanol in dichloromethane (0.5%, 1.5%, 2.5%, 4.5% and 7%, 500 ml. of each), giving 0.324 g. of a colorless foam (51%) after solvent evaporation at reduced pressure.

NMR (250 mHz, DMSO), partial: delta 0.95 (d, 6H, (Me)$_2$CH), 1.30 (s, 9H, Boc), 1.53 (s, 9H, imBoc), 5.03 and 5.07 (s, 2H ea, CBZ and benzyl ester CH$_2$), 7.2–7.5 (m, aromatic), 8.07 (s, 1H, imidazolyl C$_2$) ppm.

I.
BocPhe(N-imBoc)His-2-N-i-propylazahomocyclohexylStaLysPhe

BocPhe(N-imBoc)His-2-N-i-propylazahomocyclohexylStaLys(e-CBZ)Phe benzyl ester (265 mg., 0.211 mmol was dissolved in 11 ml. of 10:1 methanol-acetic acid with 75 mg. of 20% Pd(OH)$_2$/C (Aldrich, Pearlman's catalyst) and the mixture was shaken for 90 minutes at 25° C. under 50 p.s.i. hydrogen. The filtered mixture was concentrated, and coevaporated with toluene (3 times), and then with ether, and was dried at 56° C. for 1 hour at reduced pressure to give 228 mg. (99%) of a light yellow powder. HPLC: Dupont Zorbax 250×4.6 mm C-8 1.5 ml/min. 214 nm detection, 70/30 MeCN/pH 2.1 0.1M KH$_2$PO$_4$ buffer, retention time 4.48 minutes. A slightly more polar impurity was also produced (4.22 minutes).

NMR (250 mHz, DMSO), partial: delta 0.9–1.0 (br, isopropyl CH$_3$), 1.26, 1.28, 1.38 and 1.52 (boc singlets, evidently two major rotameric forms present), 7.4–7.0 (aromatic) ppm.

J.
BocPheHis-2-N-i-propylazahomocyclohexylStaLysPhe

BocPhe(N-imBoc)His-2-N-i-propylazahomocyclohexylStaLysPhe (200 mg., 0.183 mmol) was dissolved in methanol (2.5 ml.), and anhydrous potassium carbonate (63 mg., 0.46 mmol) was added. The mixture was stirred 90 minutes at 25° C., treated with acetic acid (200 ul.), concentrated, and evaporated to dryness at reduced pressure. The residue was dissolved in water (0.3 ml.), and treated with 30 ul. of acetic acid, 0.1 ml. methanol, and 0.015 ml. water. This solution was loaded onto a column of 15 g. Merck RP-2 silica packed in 40/60 methanol-water, and eluted with three column volumes of the same solvent. Methanol was then used to elute the title compound from the column, giving the substance after concentration and drying at reduced pressure as a pale yellow powder (122 mg., 67%). HPLC: Dupont Zorbax 250×4.6 mm C-8, 1.5 ml/min., 214 nm detection, 40/60 MeCN/pH 2.1 0.1M KH$_2$PO$_4$ buffer, retention time 9.12 minutes. An impurity was present, as identified by HPLC as above, retention time=8.12 minutes, which could be removed by chromatography on a Zorbax 9.6 mm×250 cm RP-HPLC column (C-8), in the mobile phase used above for analytical work, monitoring at 254 nm. The salts were removed by passage of the neutralized eluate concentrate through a short RP column as described above, and the thus-purified material was homogeneous in the analytical RP-HPLC system.

NMR (250 mHz, DMSO), partial: delta 1.30 (s, 9H, Boc), 0.95 (two d, 6H, NCH(Me)$_2$), 6.80 (s, 1H, imidazolyl C % proton), 7.1–7.4 (aromatic) ppm.

EXAMPLE 3

BocPheHis-2-oxahomocyclohexylStaLysPhe ($R_1=H$; $R_2=$LysPhe; and $X=O$)

A solution of BocPheHis-2-oxahomocyclohexyl-StaLysPhe methyl ester (Example 1N) (150 mg.) in methanol (2 ml.) and water (0.7 ml.) was treated at 25° C. with 109 mg. potassium carbonate, allowed to stir for 5.5 hours, and the solution was treated with 0.12 ml. acetic acid. The concentrated mixture was dissolved in acetonitrile-water (1:1) and brought to pH 6.4 with sodium hydroxide. The precipitate was collected by centrifugation, washed with water, and dried to give 70 mg. of the title compound.

NMR, proton, 250 mHz, CD$_3$OD, partial, delta, 1.35 (s, 9H, Boc), 3.7, 3.85, 4.08, 4.30 4.51 and 4.63 (m, 1H ea), 6.94 (s, 1H, imidazolyl 4-H), 7.64 and 7.68 (s, 1H total, imidazolyl 2-H in discrete conformers), 7.1–7.35 (m, 11–13H) ppm.

EXAMPLE 4

BocPheHis-2-oxahomocyclohexylStaIleRPhe ($R_1=H$; $R_2=$reduced IlePhe; $R_3=H$; and $X=O$)

A. NCO-IleR(CBZ)Phe methyl ester

By procedures analogous to those used for the synthesis of compounds in Examples 6A and 6B, BocIleR-Phe methyl ester was converted to the titled compound.

B. N-Boc-O-benzyl-2-oxahomocyclohexylStaIleR(CBZ)-Phe methyl ester

A solution of 550 mg. NCO-IleR(CBZ)Phe methyl ester and 430 mg. of (S)-3-t-butoxycarbonylamino-(R)-2-benzyloxy-4-cyclohexyl-1-butanol (Example 1J) in toluene (5 ml.) was heated at 105° C. for 11 hours, cooled, and chromatographed directly on silica eluting with ether/hexane, to give after concentration of the appropriate fractions 0.684 g. of the title urethane.

C. O-Benzyl-2-oxahomocyclohexylStaIleR(CBZ)Phe methyl ester hydrochloride

N-Boc-O-benzyl-2-oxahomocyclohexyl-StaIleR(CBZ)Phe methyl ester (672 mg.) was dissolved in 10 ml. 4N hydrogen chloride-dioxane at 25° C. and after 2 hours the mixture was concentrated, the solid coevaporated several times with ether to give a white foam, weight 0.54 g.

D. BocPhe(imBoc) O-benzyl-2-oxahomocyclohexylStaIleR(CBZ)Phe methyl ester

Following the general procedure for the synthesis of the compound in Example 2H, O-benzyl-2-oxahomocyclohexylStaIleR(CBZ)Phe methyl ester hydrochloride (520 mg.) was neutralized with triethylamine (0.123 ml.) in 2 ml. dichloromethane at 0° C. and coupled with BocPheHis(imBoc) (0.43 g.) using 196 mg. 1-hydroxybenzotriazole hydrate and 176 mg. dicyclohexylcarbodiimide for 4 hours at 0° C. then 12 hours at 20° C. giving after analogous workup 0.726 g. of the title substance as a colorless foam.

E. BocPheHis O-benzyl-2-oxahomocyclohexylStaIleR(CBZ)Phe

A solution of 530 mg. of BocPhe(imBoc) O-benzyl-2-oxahomocyclohexylStaIle R(CBZ)Phe methyl ester in 1.65 ml. of methanol was treated at 25° C. with 3 mg. potassium carbonate for 40 minutes, cooled to 0° C. and treated with 0.55 ml. water and 0.244 g. potassium carbonate, then brought to 25° C. for 46 hours 1.1 ml. water was added, and the mixture was brought to pH 4.1 with 6N hydrochloric acid. Methanol was removed by partial concentration and the aqueous solution remaining was extracted with ethyl acetate which was washed with water and dried. The concentrate was dried giving 0.45 g. of a colorless powder.

F. BocPheHis-2-oxahomocyclohexylStaIleRPhe

BocPheHis O-benzyl-2-oxahomocyclohexyl-StaIleR(CBZ)Phe (360 mg.) was shaken in 1:1 methanol-acetic acid (10 ml.) for 24 hours with 180 mg. 10% Pd/C at 25° C. and 50 p.s.i. hydrogen. The catalyst was removed by filtration through Celite, and the filtrate was concentrated to dryness giving 0.286 g. of the title substance as an amorphous powder, homogeneous by HPLC.

NMR, proton, 250 mHz, D$_4$-MeOH, partial, delta: 0.88 (m, 3–5H), 1.36 (s, 9H, Boc), 3.7, 3.87, 4.1, 4.3, 6.93 and 7.7 (m, 1H ea), 7.1–7.4 (m, 11–13H) ppm.

EXAMPLE 5

BocPheHis-2-N-i-butylazahomocyclohexylStaIleRPhe ($R_1=H$; $R_2=$reduced IlePhe; $R_3=H$; and $X=NCH_2CH(CH_3)_2$

A. (S)-3-t-butoxycarbonylamino-(R)-2-benzyloxy-4-cyclohexylbutyraldehyde

A solution of 980 mg. (S)-3-t-butoxycarbonylamino-(R)-2-benzyloxy-4-cyclohexylbutyric acid methyl ester (Ii) in dry toluene (5 ml.) was cooled and stirred at −78° C. while a solution of diisobutylaluminum hydride (DIBAL-H, 6.05 ml.) was added dropwise so that the temperature did not exceed −65° C. 15 minutes after completion of the DIBAL-H addition dry ethyl formate (0.48 ml.) was added dropwise followed by dry methanol (0.6 ml.), stirring being then continued another 15 minutes at −78° C. whereupon a 50% aqueous solution of Rochelle salts was added (10 ml.) followed by ether (50 ml.), and the mixture was brought to room temperature. The emulsion was allowed to separate and the ether layer was washed with brine, dried and concentrated to give 880 mg. (97%) of the title aldehyde which was used without further purification.

B. N-isobutyl N-[(S)-3-t-butoxycarbonylamino-(R)-2-benzyloxy-4-cyclohexyl-but-1-yl]amine A solution of (S)-3-t-butoxycarbonylamino-(R)-2-benzyloxy-4-cyclohexylbutyraldehyde (600 mg.) and isobutylammonium p-toluenesulfonate (510 mg.) were stirred together in methanol for 30 minutes at 20° C. and then treated in one portion with sodium cyanoborohydride (105 mg.). After 45 minutes 28 mg. more sodium cyanoborohydride was added and 30 minutes later the mixture was filtered through Celite, concentrated, the residue dissolved in ethyl acetate which was washed twice with aqueous bicarbonate, brine and dried over sodium sulfate. After solvent removal 600 mg. (87%) of the title amine was obtained which was used without additional purification.

C. Boc O-benzyl-2-N-i-butylazahomocyclohexyl-StaIleR(CBZ)Phe benzyl ester

The crude amine from Example 5B (600 mg.) was dissolved in 4 ml. ether and treated with 580 mg. of isocyanate (Example 4C) at 25° C., followed by 0.194 ml. triethylamine. After 1.5 hours the mixture was chromatographed on silica eluting with 1:6 ethyl acetatehexane and 0.695 g. of the title urea 5C was obtained on solvent removal of the pure fractions.

D. O-Benzyl-2-i-butylazahomocyclohexylStaIleR(CBZ)-Phe benzyl ester hydrochloride The urea, Boc O-benzyl-2-N-i-butylazahomocyclohexylStaIleR(CBZ)Phe benzyl ester was treated at 20° C. with 5 ml. 4N hydrochloric acid dioxane for 1.25 hours. Evaporation at reduced pressure followed by three coevaporations with ether and drying in vacuo gave the title amine hydrochloride 5D as a colorless amorphous solid (620 mg.).

E. BocPheHis(imBoc) O-benzyl-2-N-i-butylazahomocyclohexyl-StaIleR(CBZ)Phe benzyl ester O-Benzyl-2-i-butylazahomocyclohexyl-StaIleR(CBZ)Phe benzyl ester hydrochloride (620 mg.) was coupled to BocPheHis(imBoc) by the procedure described for the synthesis described in Example 1M, except that the reaction was then allowed to stir at 25° C. for 40 hours. Workup as described and chromatography on silica in ethyl acetate-hexane gave the desired product as a colorless amorphous foam (600 mg., 64%).

F. BocPheHis-2-N-i-butylazahomocyclohexylStaIleRPhe

A solution of 367 mg. of BocPheHis(imBoc) O-benzyl-2-N-i-butylazahomocyclohexylStaIleRPhe benzyl ester in methanol (6 ml.) and acetic acid (2.5 ml.) was shaken with 220 mg. 10% Pd/C for 23 hours at 25° C. under 50 p.s.i. hydrogen pressure, and then for 45 hours longer with 200 mg. more fresh catalyst, whereupon the mixture was filtered, concentrated, and coevaporated three times with toluene, then with ether, and dried in vacuo giving 291 mg. of an amorphous solid which was dissolved in a minimum volume of 3:1 methanol-water and loaded onto a column of Merck RP-2 silanized silica packed in 1:1 methanol-water. Elution with 1:1 methanol water (100 ml.) was followed by elution with methanol and the first 50 ml. of the 100% methanol eluant was concentrated to give 163 mg. of solid determined by NMR to be the imBoc benzyl ether derivative of the title substance. This was dissolved in 8 ml. ammonia at −78° C. and a minimal amount of excess sodium was added so that a deep blue solution was maintained. Twenty minutes later a few mg. of ammonium chloride was added and the then-colorless mixture was evaporated to a beige powder. This material was resubjected to the same reducing conditions so that the blue color persisted for 45 minutes. The ammonium chloride quenched and evaporated mixture was chromatographed on 5 g. Merck RP-2 silica eluting with 1:1 methanol-water containing 1% HOAc (50 ml.) then with 100% methanol. The separation of the major most polar substance from more lipophilic impurities was monitored by RP-HPLC, and evaporation of the appropriate 1:1 fractions gave 53 mg. of a solid which was dissolved in 0.5 ml. dichloromethane and treated with 5 ml. ether. The precipitate was separated and the supernatant evaporated leaving 16 mg. of the title substance which was pure by RP-HPLC analysis.

NMR, proton, 250 mHz, DMSO, partial, delta, 0.72 (d, J=7 Hz, 3H), 0.78 (m, 9H), 1.30 (s, 9H, Boc), 3.87, 4.16, 4.55, 6.22 and 8.36 (m, 1H, ea), 6.86 and 7.54 (s, 1H ea, imidazolyl CH), 7.1 (d, 1H), 7.15–7.35 (m, 11–13H) ppm.

EXAMPLE 6

BocPheHis-2-azahomocyclohexylStaIleRPhe ($R_1$=H; $R_2$=reduced IlePhe; $R_3$=H; and X=NH)

A. BocIleR(CBZ)Phe benzyl ester

A solution of BocIle RPhe benzyl ester (15.0 g.) in dioxane (100 ml.) and water (50 ml.) was cooled to 6° C., and 6N sodium hydroxide was added to bring the pH to 13. Benzyl chloroformate (6.1 ml.) was added in one portion and the pH was maintained at 10 by addition of 6N sodium hydroxide. When addition of base was no longer necessary, another 1 ml. CBZ-Cl was added and pH 10 maintained. After a few minutes at 5° C., the mixture was concentrated, the residue extracted with ether, washed with aqueous bicarbonate, brine, dried, concentrated, and the solid residue was recrystallized from 100 ml. hexane, giving 17.1 g. of the title product, mp 85°–88° C.

B. NCO-Ile R(CBZ)Phe benzyl ester

A solution of BocIleR(CBZ)Phe benzyl ester, 3.31 g., in dry toluene (11 ml.) was treated sequentially at 25° C. with triethylamine, 1.17 ml., and trichlorosilane (0.79 ml.) and heated with stirring at 80° C. under nitrogen for 1.7 hours. The mixture was cooled, treated with triethylamine (10 ml.) and ether (125 ml.), filtered through Celite, and concentrated. The procedure was repeated with additional amounts of triethylamine and ether until a clear yellow oil was obtained (2.95 g.) which was used without additional purification.

C. N-t-Boc-O-t-butyldimethylsilyl-2-azahomocyclohexyl-StaIleR(CBZ)Phe benzyl ester The compounds of Examples 2D (521 mg.) and 6B (669 mg.) were mixed together in 4 ml. toluene at 25° C. After 15 minutes 80 mg. more 6B was added, and after 1 hour at 25° C. and 18 hours at 0° C. the mixture was chromatographed on silica eluting with ethyl acetate/-hexanes. The title compound was isolated as a colorless foam, 0.89 g., after solvent removal in vacuo of the appropriate fractions.

D. 2-AzahomocyclohexylStaIleR(CBZ) benzyl ester hydrochloride

The product of Example 6C (820 mg.) was dissolved at 25° C. in 4N hydrochloric acid dioxane, and after 2 hours the mixture was concentrated to dryness, and coevaporated several times with added ether, giving after drying in vacuo a pale yellow foam, 0.56 g.

E. BocPheHis(imBoc)-2-azahomocyclohexyl-StaIleR(CBZ)Phe benzyl ester

Using the procedure of Example 2H, the product of Example 6D, 0.523 g., was neutralized with 0.13 ml. triethylamine in 1.5 ml. dichloromethane at 0° C. and coupled with BocPheHis(imBoc), 0.445 g., using 0.204 g. 1-hydroxybenzotriazole and 0.183 g. dicyclohexylcarbodiimide for 4 hours at 0° C. and 12 hours at 25° C. The analogously isolated title substance (0.479 g.) was an amorphous colorless foam.

F. BocPheHis(imboc) 2-azahomocyclohexylStaIleRPhe

The compound 6E (453 mg.) was shaken with 80 mg. 20% Pd(OH)2/C in 10:1 methanol-acetic acid under 50 p.s.i. hydrogen for 3 hours. The filtered solution was concentrated, coevaporated with toluene several times to give 0.354 g. of a brown foam.

G. BocPheHis-2-azahomocyclohexylStaIleRPhe

BocPheHis(imBoc)-2-azahomocyclohexylStaIeRPhe (319 mg.) was dissolved in 7 ml. methanol and treated with 120 mg. of potassium carbonate for 1 hour at 25° C. 3 ml. acetic acid was added and the mixture was concentrated. The title substance was obtained after passage of the oil through a Merck RP-2 column in methanol/water containing acetic acid to remove inorganic salts. Concentration gave 225 mg. of a solid which was dissolved in dichloromethane and precipitated by addition of 2 volumes ether. The solid was collected by centrifugation and dried 137 mg.

NMR, proton, 250 mHz, DMSO, partial, delta: 0.72 (d, 3H, J=7 Hz), 0.82 (m, 3H), 1.30 (s, 9H, Boc), 3.86, 4.17, 4.53, 5.90 and 7.40 (m, 1H ea), 6.15, 7.07 and 8.24 ppm.

EXAMPLE 7

BocPheHis-2-azahomocyclohexylStaLysPhe ($R_1$=H; $R_2$=LysPhe; and X=NH)

A. N-t-Boc-O-t-butyldimethylsilyl-2-azahomocyclohexyl-StaLys(CBZ)Phe benzyl ester The procedure of Example 2F was followed. Thus, the compound of Example 2D, 0.454 g., and Lys(CBZ)-Phe benzyl ester were coupled using 0.20 ml. triethylamine, 4.5 ml. total dichloromethane, 0.1 g. imidazole, and 0.239 g. carbonyldiimidazole first at 0° C. then at 25° C. for 18 hours, and after analogous workup and chromatography the title substance was isolated as a colorless foam, 0.674 g.

B. 2-AzahomocyclohexylStaLys(CBZ)Phe benzyl ester hydrochloride

The product of Example 7A, hydrogen chloridedioxane (5 ml.) were stirred together for 2.5 hours at 25° C. The solution was evaporated to give after several coevaporations with ether and drying in vacuo overnight, 0.65 g. of the title salt as a pale yellow amorphous solid.

C. BocPheHis(imBoc)-2-azahomocyclohexyl-StaLys(CBZ)Phe benzyl ester

The procedure used for the synthesis of 2H was followed. Thus, 0.622 of the compound of Example 7B was neutralized at 0° C. with triethylamine (0.147 ml.) in 4 ml. dichloromethane and coupled to BocPheHis-(imboc), 0.43 g., using 0.2 g. and dicyclohexylcarbodiimide, 0.18 g. The analogously isolated title substance, 0.35 g., was a colorless amorphous solid.

D. BocPheHis(imBoc)-2-azahomocyclohexylStaLysPhe

The compound of Example 7C (340 mg.) was shaken under 50 p.s.i. with 75 mg. 20% Pd(OH)2/C in 16 ml. 10:1 methanol/acetic acid for 3.5 hours, filtered, and concentrated to give 247 mg. of a powder.

E. BocPheHis-2-azahomocyclohexylStaLysPhe

The compound of Example 7D was dissolved in methanol, 4 ml. and treated at 25° C. with 92 mg. potassium carbonate for 45 minutes, 0.19 ml. acetic acid was added and the residue after concentration and evaporation of all acetic acid was dissolved in 20 ml. 3:1 methanol acetic acid, and adjusted to pH 6.6 with sodium hydroxide. The concentrated residue was dissolved in water, and the insoluble solid was filtered and dried overnight giving 230 mg of the title substance.

NMR, proton, 250 mHz, DMSO, partial, delta: 1.28 (s, Boc), 7.0, 7.58, 8.20, 8.39, 8.97 (m, 1H ea), 7.1–7.4 (m, 12–14H) ppm.

EXAMPLE 8

BocPheHis-2-i-butylazahomocyclohexylStaLysPhe ($R_1$=H; $R_2$=LysPhe, and X=NCH$_2$CH(CH$_3$)$_2$)

A. N-isobutyl-N-[3-(S)-N-t-butoxycarbonylamino-2(R)-t-butyldimethylsilyloxy-4-cyclohexylbut-1-yl] amine Primary amine from Example 2D (4.78 g.) was dissolved in 50 ml. dry methanol and treated sequentially at 20° C. with acetic acid (3.5 ml.), 3 angstrom 600 mesh molecular sieves (2 g.), sodium cyanoborohydride (1.18 g.), and finally dropwise with isobutyraldehyde (1.71 ml.). Another portion after 20 minutes the mixture was filtered through Celite, concentrated, and dissolved in ethyl acetate which was washed with aqueous bicarbonate. Drying and concentration give 5.70 g. of the title amine as a colorless syrup which was used without further purification.

B. N-t-Boc-O-t-butyldimethylsilyl-2-N-isobutylazahomocyclohexylStaLys(e-CBZ)Phe benzyl ester The procedure for the synthesis of Example 2F was followed, using 840 mg. of the amine from Example 8A, 162 mg. imidazole, 390 mg. carbonyldiimidazole, 1.32 g. LysPhe(CBZ)OBn hydrochloride and 333 ul. of triethylamine in total 10.5 ml. dichloromethane for 18 hours at 25° C. giving after extraction and silica chromatography in ethyl acetate-hexane 1.32 g. (71%) of the title urea.

C. 2-N-i-butylazahomocyclohexylStaLys(e-CBZ)Phe benzyl ester

The product of Example 8B (1.25 g.) was dissolved at 0° C. in 12 ml. 4N hydrogen chloride-dioxane and the solution was brought to 25° C. After 2.5 hours the solution was concentrated and the residue was dried in vacuo (1.15 g.). This solid was dissolved in 6 ml. of dry acetonitrile and treated dropwise at 0° C. with 1.0 ml. hydrogenfluoride/pyridine. After 3 hours the mixture was poured into an ice-cold stirred mixture of ethyl acetate and 2N sodium hydroxide (60 ml.). The organic layer was separated, dried and concentrated giving 840 mg. of the title aminoalcohol.

D. BocPheHis(imBoc)-2-N-isobutylazahomocyclohexyl-StaLys(e-CBZ)Phe benzyl ester The product from Example 8C (800 mg.) was coupled to BocPheHis(imBoc) as in the preparation of 1M except that triethylamine was omitted, and the title compound was isolated analogously (567 mg., 44%).

E. BocPheHis(imBoc)-2-N-isobutylazahomocyclohexyl-StaLysPhe

The product of Example 8D (550 mg.) was dissolved in methanol (15 ml.) and acetic acid (5 ml.) and shaken with 100 mg. 10% Pd/C at 40 p.s.i. hydrogen and 25° C. for 2.5 hours. The mixture was filtered, concentrated, coevaporated twice with toluene, twice with ether, suspended in ether, and filtered. The filtered solid was dried in vacuo, weight 428 mg.

F. BocPheHis-2-i-butylazahomocyclohexylStaLysPhe

The product of Example 8E (391 mg.) was dissolved in 5 ml. methanol and 121 mg. potassium carbonate and 1 ml. water were added sequentially at 25° C. After 30 minutes the pH was brought to 6.6 with 1N HCl and the mixture was concentrated at reduced pressure to dryness. The solid was dissolved in 5 ml. methanol and water was added dropwise until precipitation appeared complete (15 ml.). The insoluble oil was collected by centrifugation and washed twice with 20% aqueous methanol. The residue was dried in vacuo and coevaporated several times with ether to give 200 mg. of a solid which was purified by RP-HPLC in the following system: 1 cm×250 mm Zorbax C-8 column, 48/52 acetonitrile/pH 4.3 0.2M ammonium acetate/acetic acid buffer, 6.3 ml./min., 254 nm detection. Injections were 5 mg. each in 0.1 ml. mobile phase. The pure fractions were concentrated to dryness giving 12 mg. of the product of Example 8F for each 25 mg. of the crude solid injected.

NMR, proton, 250 mHz, DMSO, partial, delta: 0.75 (d, 6H), 1.31 (s, 9H, Boc), 3.84, 4.52, 6.28 (m, 1H ea), 4.11 (m, 2-3H), 6.8 and 7.45 (s, 1H ea, imidazolyl CH), 7.7 and 8.36 (d, 1H ea, J=8 Hz), 7.1-7.35 (m, 12-14H) ppm.

EXAMPLE 9

BocPheHis-2-cyclohexylmethylazahomocyclohexyl-StaIleRPhe ($R_1$=H; $R_2$=reduced IlePhe; $R_3$=H; and X=$NCH_2C_6H_{11}$

A. N-Cyclohexylmethyl-N-[3(S)-N-t-Butoxycarbonylamino-2(R)-t-butyldimethylsilyloxy-4-phenylbut-1-yl] amine The product of Example 2A was reductively coupled to cyclohexanecarboxaldehyde according to the procedure for the synthesis of the product of Example 2E, giving the title substance in near quantitative yield, which was used without additional purification.

B. N-Cyclohexylmethyl-N-[3(S)-N-t-Butoxycarbonylamino-2(R)-t-butyldimethylsilyloxy-4-phenylbut-1-yl] trifluoroacetamide The product of Example 9A, 4.3 g., was allowed to react at 0° C. in 25 ml. dichloromethane and 1.55 ml. 2,6-lutidine with 1.37 ml. trifluoroacetic anhydride for 15 minutes. The solution was washed with 1N hydrochloric acid, water, dried over magnesium sulfate, concentrated and chromatographed on silica eluting with ethyl acetate/hexanes to give 3.16 g. of the title amide.

C. N-Cyclohexylmethyl N]3(S)-N-t-Butoxycarbonylamino-2(R)-t-butyldimethylsilyloxy-4-cyclohexylbut-1-yl] trifluoroacetamide The product of Example 9B, 3.05 g., was hydrogenated in 35 ml. methanol with 340 mg. 10% Rh/C for 24 hours, then again with 120 mg. added catalyst for another 24 hours, and the filtered and concentrated product was chromatographed on silica eluting with ethyl acetate/hexanes giving 2.76 of a colorless foam.

D. N-Cyclohexylmethyl N-[3(S)-N-t-Butoxycarbonylamino-2(R)-t-butyldimethylsilyloxy-4-cyclohexylbut-1-yl]amine The product of Example 9C was dissolved in 20 ml. abs. ethanol with 350 mg. sodium borohydride at 55° C. for 2.2 hours. The solution was concentrated, the residue dissolved in 100 ml. ether which was washed with 25 ml. 1N sodium hydroxide, water, dried over sodium sulfate and evaporated giving 2.2 of the title substance as a colorless syrup.

E. N-t-Boc-O-t-butyldimethylsilyl-2-cyclohexylmethylazahomocyclohexylStaIleR(CBZ)Phe benzyl ester By the procedure used in the synthesis of Example 6C, 0.60 g. of the product of Example 9D was allowed to react with 1.4 equivalent of the product of Example 6B in toluene at 25° C. (triethylamine, 2 equivalent was added here) for 2 hours and the product isolated analogously, weight 294 mg.

F. 2-CyclohexylmethylazahomocyclohexylStaIleR(CBZ)-Phe benzyl ester

The product of Example 9E, 0.69 g., was treated with 4 ml. 4N hydrogen chloride-dioxane for 1.3 hours, evaporated, and coevaporated with ether several times to give after drying 0.55 g. of a foam.

G. BocPheHis(imBoc)2-N-cyclohexylmethylazahomocyclohexylStaIleR(CBZ)Phe benzyl ester The general procedure of Example 2H was used to couple 0.53 g. of the product of Example 9F by triethylamine (0.115 ml.) neutralization in 5 ml. dichloromethane at 0° C. with BocPheHis(imBoc) (0.353 g.) using 1-hydroxybenzotriazole, 0.16 g., and 0.145 g. dicyclohexylcarbodiimide at 0° C. for 4 hours and 20° C. for 15 hours, producing the title substance (0.679 g.) after analogous workup.

H.
BocPheHis(imBoc)-2-N-cyclohexylmethylazahomocyclohexylStaIleRPhe benzyl ester Hydrogenation (50 p.s.i.) of the product of Example 9G, 265 mg., with 75 mg. 20% Pd(OH)$_2$/C in 11 ml. 1:10 acetic acid-methanol for 1.8 hours followed by filtration, concentration, coevaporation with ether, and drying gave 213 mg. of the title substance.

I.
BocPheHis-2-N-cyclohexylmethylazahomocyclohexylStaIleRPhe

Dissolution of the product of Example 9H, 0.19 g., in methanol with 72 mg. potassium carbonate at 25° C. for 0.5 hour, followed by addition of acetic acid (0.45 ml.), concentration, and passage of the residue through a 15 g. column of Merck RP-2 gel in Methanol-water to remove salts gave 122 mg. of the title substance.

NMR, proton, 250 mHz, DMSO, partial, delta: 0.7 (d, 3H, J=7 Hz), 0.8 (t, 3H), 1.3 (s, 9H, boc), 3.87, 4.14, 4.54, 6.27, 7.49 and 8.38 (m, 1H ea), 6.86 and 7.52 (s, 1H ea, imidazolyl CH), 7.1–7.4 (m, 11–13H) ppm.

Example 10

BocPhe-N-methylHis-2-N-i-butylazahomocyclohexylStaLysPhe ($R_1$=CH$_3$; $R_2$=lysPhe; and X=NCH$_2$CH(CH$_3$)$_2$)

A. N-Methyl-L-Histidine methyl ester

One gram of N-methyl-L-histidine was dissolved in methanol and HCl was bubbled in at 0° C. for a few minutes. The mixture was heated at reflux 1.5 hours (more hydrochloric acid was introduced on several occasions) and the cooled solution was concentrated at reduced pressure. HPLC indicated about 7% of unreacted starting material remaining. The product was not additionally purified.

B. BocPhe-N-methylHis methyl ester

N-Methyl-L-histidine methyl ester (1.05 g.) was dissolved in dichloromethane and at 0° C. 1.25 ml. triethylamine was added, followed by N-t-Boc-L-phenylalanine (1.14 g.), 1-hydroxybenzotriazole hydrate (1.04 g.), and dicyclohexylcarbodiimide (0.89 g.). The mixture was stirred at 0° C. and allowed to slowly warm to 20° C. over a 4–5 hour period where it was stirred an additional 10 hours. The slurry was filtered, concentrated, redissolved in ethyl acetate (100 ml.), the additional precipitate was filtered, and the filtrate was washed with 1N sodium hydroxide (2×10 ml.), dried over magnesium sulfate, and concentrated to give 0.84 g. of an off-white solid. Recrystallization of this material from ethyl acetate gave 0.47 g. of the title compound as a colorless powder. Additional material was obtained as follows. The combined filtered drying agent and second (from ethyl acetate) precipitate above were heated in methanol, and the resultant suspension was cooled, filtered, and the filtrate was concentrated to give a solid which was chromatographed on silica in ethanol-dichloromethane to give 0.857 g. of the pure title substance.

C. BocPhe-N-methylHis(imBoc)

The product of Example 10B, 2.32 g. was dissolved in acetone (70 ml.) and water (20 ml.) and the solution was cooled to 0° C. and treated with 5.4 ml. of 1N sodium hydroxide. After 3.3 hours at 0° C. and 15 hours at −20° C. the mixture was partially concentrated, and the remaining aqueous solution was adjusted to pH 5.8 with 1N hydrochloric acid. The free acid did not precipitate, so the pH was adjusted to 11 with 6N sodium hydroxide and the volume was adjusted to 30 ml. with water. Dioxane (30 ml.) was added, and the mixture while being cooled at 0° C. was treated with di-t-butyldicarbonate (1.61 ml.) and the pH was kept between 9 and 11 with added 6N sodium hydroxide. After about 1 hour at 0° C. the cooling bath was removed and 0.5 ml. di-ti-butyldicarbonate was added. Fifteen minutes later the mixture was partially concentrated, extracted with ethyl acetate which was washed with water, the aqueous layers separated, combined, mixed with fresh ethyl acetate and brought to pH 1.4 with 6N hydrochloric acid at 0° C. The layers were separated, the organic one washed with water, dried over sodium sulfate and concentrated, and the resultant oil homogenized as an amorphous foam (1.9 g.) by several coevaporations with added ether. The title substance was over 95% pure by RP-HPLC.

D. BocPhe-N-methylHis(imBoc)-2-N-i-butylazahomocyclohexylStaLys(CBZ)Phe benzyl ester The product of Example 8C (786 mg.) was coupled with the product from Example 10D (567 mg.) in dichloromethane (no triethylamine was added) with dicyclohexylcarbodiimide at 0° C. and 1-hydroxybenzotriazole at 0° C. for 5 hours and 25° C. for 12 hours according to the procedure described for the synthesis of 2H. The pure title substance (265 mg.) was isolated analogously together with another 373 mg. of desired material contaminated with a slightly more polar impurity. The first (pure) fraction was used substantially.

E. BocPhe-N-methylHis(imBoc)-2-N-i-butylazahomocyclohexylStaLysPhe

The product of Example 10D, 265 mg., was dissolved in 15 ml. methanol and 3 ml. acetic acid and shaken with 80 mg. 10% Pd/C under 40 p.s.i. hydrogen pressure for 2 hours at 25° C. The mixture was filtered, coevaporated with toluene, ether (thrice) and dried in vacuo to give 238 mg. of the title acid.

F. BocPhe-N-methylHis-2-N-i-butylazahomocyclohexylStaLysPhe

The product of Example 10E (230 mg.) was dissolved in 5 ml. methanol and treated with 0.6 ml. 1N sodium hydroxide at 0° C. The mixture was rapidly brought to 25° C. and 4 ml. water was added. The pH was adjusted to 7 with added hydrochloric acid and the mixture was concentrated, taken up in 1:1 acetonitrile/pH 4.0 0.1M ammonium acetate buffer, filtered through a 0.5 um filter, and purified by repeatedly injecting 250 ul. aliquots of this solution onto the following HPLC system: Dupont Zorbax C-8, 9.8 mm×25 cm. 50/50 acetonitrile/pH 4.0 0.1M ammonium acetate, 6.3 ml./min., 254 nm detection. The desired substance (4.65 min.) was separated from an earlier eluting impurity. The fractions were concentrated, and lyophilized overnight at 25° C., and the resultant solid was brought to constant weight in vacuo at 56° C., leaving 88 mg. of the pure title substance.

NMR, proton, 250 mHz, DMSO, partial, delta: 0.7 (m, 6–8H), 1.30 (s, Boc, 9H), 4.52, 5.17, 6.2 (m, 1H ea), 6.84 and 6.7 (s, 1H total, imidazolyl 4-H in rotameric isomers), 7.4 (s, integral uncertain, imidazolyl 2-H), 7.73 (m, 2H), 7.1–7.2 (m, 12–14H) ppm.

EXAMPLE 11

BocPhe-N-methylHis-2-N-i-butylazahomocyclohexyl-StaLysPheNH$_2$ (R$_1$=CH$_3$; R$_2$=LysPheNH$_2$; X=NCH$_2$CH(CH$_3$)$_2$

A.
BocPhe-N-methylHis-2-N-i-butylazahomocyclohexyl-StaLys(CBZ)Phe methyl ester The product of Example 10D, 332 mg., was dissolved in 2.5 ml. methanol and 4 mg. potassium carbonate was added at 25° C. After 1 hour 9 mg. more potassium carbonate was added and the mixture was stored at −20° C. overnight. The residue after concentration was dissolved in ethyl acetate, washed with 4 ml. water, dried over magnesium sulfate, filtered, and concentrated to give after drying in vacuo 265 mg. of a colorless solid.

B.
BocPhe-N-methylHis-2-N-i-butylazahomocyclohexyl-StaLys(CBZ)Phe NH$_2$

The product of Example 11A, 249 mg., was dissolved in methanol (3 ml.), and the resulting solution was cooled to 0° C. and saturated with ammonia gas. 3 angstrom molecular sieves 0.5 g., (600 mesh) were added, followed by ammonium acetate (2 mg.) and the vessel was tightly stoppered and brought to 25° C. for 72 hours. The filtered mixture was concentrated, evaporated and taken in vacuo to constant weight, giving 267 mg. of a yellow amorphous powder.

C.
BocPhe-N-methylHis-2-N-i-butylazahomocyclohexyl-StaLysPheNH$_2$

The product of Example 11B, 230 mg., was shaken with 75 mg. 20% Pd(OH)$_2$/C under 50 p.s.i. hydrogen at 25° C. in 11 ml. 10/1 methanol-acetic acid for 1 hour. The filtered mixture was concentrated, coevaporated three times each with toluene, then ether, dried in vacuo at 56° C. for 0.5 hour and overnight at 25° C. giving 196 mg. of an off-white powder. The substance was purified by preparative RP-HPLC using a 9.8×250 mm Zorbax C-8 column in 50/50 acetonitrile/pH 4.3 0.1M ammonium acetate at 6.3 ml./min. and 254 nm detection. Approximately 30% recovery was obtained of crude material injected (60 mg. gave 18 mg. pure product after concentration of appropriate fractions and further drying in vacuo).

NMR, proton, 250 mHz, DMSO, partial, delta 0.6–0.85 (m, 7–9H), 1.32 (boc, s, 9H), 2.78, 3.02 (both s, 3H total N—CH$_3$ of two rotameric forms), 6.8 and 6.9 (s, 1H total), 7.1–7.4 (m, 12–13H), 7.45 (s, 1H) ppm.

EXAMPLE 12

BocPheHis-2-N-(6-aminohexyl)azahomocyclohexyl-StaIleRPhe (R$_1$=H; R$_2$=reduced IlePhe; R$_3$=H; and X=N(CH$_2$)$_6$NH$_2$)

A. 6-Benzyloxycarbonylaminohexanol

This substance was prepared in quantitative yield by diisobutylaluminum hydride reduction of 6-benzylcarbonylaminohexanoic acid methyl ester according to the procedure described in Example 5A.

B.
N-[(6-Benzyloxycarbonylamino)hex-1-yl]-N-[(S)-3-t-butoxycarbonylamino-(R)-2-benzyloxy-4-cyclohexyl-but-1-yl]amine According to the procedure of Example 2E, the amine product of Example 2D was reductively aminated with 1.3 equivalent of the product of Example 12A, and the title product was analogously isolated in quantitative yield.

C.
N-t-Boc-O-t-butyldimethylsilyl-2-N-(6-CBZ-aminohexyl)azahomocyclohexylStaIleR(CBZ)Phe benzyl ester By the procedure used in Example 6C, 1.64 g. of the product from Example 12B was allowed to react with 1.2 equivalent of the product from Example 6B in toluene at 25° C. for 1 hour and the product isolated analogously, weight 1.36 g.

D. 2-N-(6-CBZ-aminohexyl)azahomocyclohexylStaIle R(CBZ)Phe benzyl ester hydrochloride The product in 10 ml. 4N hydrogen chloride-dioxane at 25° C. for 45 minutes and concentrated. The residue was coevaporated with ether several times and dried in vacuo giving 1.1 g. colorless foam.

E.
BocPheHis(imBoc)-2-N-(6-CBZ-aminohexyl)azahomocyclohexylStaIleR(CBZ) benzyl ester The procedure of Example 2H was used to couple 0.85 g. of the product of Example 12D with 0.534 g. BocPheHis(imBoc), giving after analogous purification 0.88 g. of the title substance as a colorless foam.

F.
BocPheHis(imBoc)-2-N-(6-aminohexyl)azahomocyclohexylStaIleRPhe

Hydrogenation (50 p.s.i.) of the product of Example 12E, 433 mg., with 100 mg. 20% Pd(OH)$_2$/C in 20 ml. 1:10 acetic acid-methanol for 1.8 hours followed by filtration, concentration, coevaporation with ether, and drying gave 210 mg. of the title substance.

G.
BocPheHis-2-N-(6-aminohexyl)azahomocyclohexyl-StaIleRPhe

The product of Example 12F, 187 mg., was dissolved in 2 ml. methanol and 66 mg. potassium carbonate was added after 45 minutes 0.5 ml. acetic acid was added and the mixture was evaporated to a powder. The major title substance could be separated from a less and a more polar impurity and thus obtained in pure form by preparative RP-HPLC under the chromatographic conditions used to purify the product of Example 11E. Purification of 27 mg. of the above solid gave 9 mg. of pure product.

NMR, proton, 250 mHz, DMSO, partial, delta: 0.7 (d, 3H), 0.82 (t, 3H), 1.32 (s, 9H, Boc), 3.84, 4.18, 4.57 (m, 1H ea), 6.87 and 7.49 (s, 1H ea, imidazolyl CH), 7.14–7.4 (m, 11–13H) ppm.

EXAMPLE 13

BocPheHis-2-N-i-butylazahomocyclohexylStaIle R(6-aminohexyl)Phe ($R_1$=H; $R_2$=reduced IlePhe; $R_3$=(CH$_2$)$_6$NH$_2$; and X=NCH$_2$CH(CH$_3$)$_2$)

The product of Example 14F (88 mg.) was dissolved in methanol (20 ml.) and about 1 g. of anhydrous ammonia was introduced. This solution was shaken with 5% Rh/C (70 mg.) for 6 hours at 25° C. and 50 p.s.i. hydrogen, 40 mg. more 5% Rh/C was added and the mixture was hydrogenated as above for 18 hours longer. Filtration of the catalyst, concentration, trituration of the resultant 102 mg. solid with several portions of 2:1 ether/hexane gave after drying to constant weight 73 mg. of the pure title substance as a colorless powder.

NMR, proton, 250 mHz, CD$_3$OD, partial, delta: 0.87 (m, 12–14H), 1.34 (Boc, s, 9H), 2.68, 3.67, 3.76, 3.98, 4.22, 4.58 (m, 1H ea), 6.9 and 7.6 (s, 1H ea, imidazolyl C—H), 7.1–7.4 (m, 11–13H) ppm.

EXAMPLE 14

BocPheHis-2-N-i-butylazahomocyclohexylStaIleR-(5-cyanopentyl)Phe ($R_1$=H; $R_2$=reduced IlePhe; $R_3$=(CH$_2$)$_5$CN; and X=CH$_2$CH(CH$_3$)$_2$)

A. BocIleR(5-cyanopentyl)Phe benzyl ester

A solution of BocIleRPhe benzyl ester (3.57 g.) in methanol (32 ml.) and acetic acid (2.3 ml.) was treated sequentially with 3 angstrom 600 mesh molecular sieves (1.7 g.) sodium cyanoborohydride (0.95 g.) and then dropwise with 5-formylvaleronitrile (1.05 g.) at 25° C. After 1 hour 0.25 g. sodium cyanoborohydride was added followed by 0.4 g. 5-formylvaleronitrile, and after 0.5 hour the mixture was filtered through Celite, diluted with ethyl acetate, and washed twice with 200 ml. saturated aqueous sodium bicarbonate. 300 ml. 1N sodium hydroxide was added to the aqueous phase which was then extracted with ethyl acetate, and the combined organic layers were washed with aqueous bicarbonate, water, brine, and dried sodium sulfate to give after concentration a yellow oil which was chromatographed on silica eluting with ethyl acetate/hexanes to give 4.29 g. of the title nitrile as a colorless syrup.

B. IleR(5-cyanopentyl)Phe benzyl ester

The product of Example 14A, 1.2 g. was treated at 0° C. with 20 ml. 4N hydrogen-chloride dioxane and the solution was brought to 25° C. for 1 hour. The solvent was removed and the residue repeatedly coevaporated with added ether to give 1.13 g. of the hydrochloride as a pale yellow amorphous powder.

C. N-t-Boc-O-t-butyldimethylsilyl-2-N-i-butylazahomocyclohexylStaIleR(5-cyanopentyl)Phe benzyl ester The procedure of Example 2F was followed using 1.73 g. of the product of Example 14B, 0.92 ml. triethylamine in 10 ml. dichloromethane, and 1.15 g. of the product of Example 8A, 0.63 g. carbonyldiimidazole, and imidazole (0.225 g.) in 20 ml. dichloromethane for 72 hours at 25° C. The analogously isolated title substance (1.36 g.) was a colorless syrup.

D. 2-N-i-ButylazahomocyclohexylStaIleR(5-cyanopentyl)Phe benzyl ester

The product of Example 14E, 610 mg., was dissolved in 18 ml. acetonitrile, cooled to 0° C., and treated with 4 ml. 48% aqueous hydrofluoric acid. After 3 hours the mixture was diluted with ethyl acetate and washed three times with saturated aqueous bicarbonate, water and brine. The dried sodium sulfate solution was concentrated to give 0.5 g. of the title aminoalcohol as a yellow oil.

E. BocPheHis(imBoc)-2-N-i-butylazahomocyclohexylStaIleR(5-cyanopentyl)Phe benzyl ester The product of Example 14D, 0.50 g., was coupled to BocPheHis(imBoc) (0.425 g.) using 2.5 ml. dichloromethane, 0.027 ml. triethylamine, 180 mg. 1-hydroxybenzotriazole and 174 mg. dicyclohexylcarbodiimide for 72 hours at 0° C., according to the procedure for the synthesis of Example 2H. The analogously isolated title substance was a syrup (0.650 g.).

F. BocPheHis(imBoc)-2-N-i-butylazahomocyclohexylStaIleR(5-cyanopentyl)Phe

The product of Example 14E, 292 mg., was dissolved in 6 ml. methanol and 1 ml. acetic acid and shaken with 20% Pd(OH)$_2$/C (80 mg., Pearlman's catalyst) for 2 hours at 25° C. and 50 p.s.i. hydrogen. The filtered mixture was evaporated and coevaporated with toluene to give after drying in vacuo 253 mg. of the title substance as a light orange solid.

G. BocPheHis-2-N-i-butylazahomocyclohexylStaIleR(5-cyanopentyl)Phe

The product of Example 14F, 50 mg., was dissolved in 10 ml. methanol and was treated at 25° C. with 0.15 ml. sodium hydroxide for 1 hour. The solution was adjusted with 1N hydrochloric acid to pH 6.6 and concentrated to give a white solid which was dissolved in 4 ml. 10/7 methanol/water and passed through a 5 g. column of RP-silica, eluting first with 3 column volumes of 10/7 then 5 column volumes of 100/0 methanol/water. The initial methanol fractions were concentrated giving 27 mg. of pure product as a colorless solid.

NMR, proton, 250 mHz, CD$_3$OD, partial, delta, 0.88 (m, 12–14H), 1.48 (s, 9H, Boc), 2.44 (t, 2H, J=7H), 3.86, 4.0, 4.21, 4.57 (m, 1H ea), 6.92 and 7.62 (s, 1H ea, imidazolyl CH), 7.1–7.5 (m, 12–14H) ppm.

EXAMPLE 15

BocPheNle-2-N-i-butylazahomocyclohexylStaLysSta ($R_4$=CH$_2$CH(CH$_3$)$_2$)

A. N-t-Butoxycarbonyl Statine benzyl ester

Boc-Statine, 8.83 g., was dissolved in dry dimethylformamide and treated at 25° C. for 4.5 hours with 4.43 g. potassium carbonate and 3.81 ml. benzyl bromide. The mixture was concentrated in vacuo, 500 ml. ethyl acetate was added and the suspension was washed with saturated aqueous lithium chloride (2×50 ml.), water (5×50 ml.), dried magnesium sulfate, filtered and concentrated to give 11.8 g. of a yellow syrup which was used without further purification.

B. Statine benzyl ester hydrochloride

The product of Example 15A, 11.7 g., was dissolved in 40 ml. 4N hydrogen chloride-dioxane for 45 minutes at 25° C., concentrated, coevaporated with added ether three times, and dried in vacuo to constant weight, giving 9.87 g. of a brown foam which was used without additional purification.

C. BocLys(CBZ)Sta benzyl ester

The product from Example 15B, 4.94 g., was dissolved in dichloromethane (40 ml.), cooled to 0° C., treated sequentially with 2.96 ml. triethylamine, 6.24 g. Na-Boc(e-CBZ)L-Lysine, 3.77 g. 1-hydroxybenzotriazole, and 3.38 g. dicyclohexylcarbodiimide. After being stirred at 0° C. for 5 hours and 20° C. for 30 hours, the mixture was filtered, concentrated, dissolved in ethyl acetate, filtered, the filtrate washed with 3×30 ml. 1N sodium hydroxide, water, dried over magnesium sulfate, concentrated, and chromatographed on silica eluting with an ethanol-methylene chloride gradient giving after concentration of the appropriate fractions 7.5 g. of the title compound as a colorless foam.

D. Lys(e-CBZ)Sta benzyl ester

The product of Example 15C, 7.5 g., was dissolved in 40 ml. 4N hydrogen chloride-dioxane for 2 hours at 25° C., concentrated and dried in vacuo to constant weight to give 6.6 g. of a colorless foam.

E. N-t-Boc-O-t-butyldimethylsilyl-2-N-i-butylazahomocyclohexylStaLys(e-CBZ)Sta benzyl ester The product of Example 8A, 1.8 g., was coupled to 2.39 g., of the product of Example 15D, according to the procedure of Example 2E, using 15 ml. dichloromethane, 1.02 g. carbonyldiimidazole, 350 mg. imidazole and 0.71 ml. triethylamine at 0° C. for 7 hours and 25° C. for 14 hours. The analogously isolated title substance weighed 2.04 g.

F. 2-N-i-ButylazahomocyclohexylStaLys(e-CBZ) Sta benzyl ester hydrochloride

The product of Example 15E, 1.93 g., was dissolved at 25° C. in 9 ml. acetonitrile and 1 ml. aqueous 48% hydrofluoric acid was added. After 45 minutes 1 g. sodium bicarbonate was added, and after effervescence ceased the mixture was concentrated at reduced pressure. The residue was dissolved in water which was extracted with ethyl acetate. The combined organic layers were washed with water, dried over magnesium sulfate, filtered, concentrated, and evaporated in vacuo to constant weight (1.68 g.). This residue was dissolved in 5 ml. 4N hydrogen chloride-dioxane for 45 minutes at 25° C. concentrated, coevaporated several times with ether and dried in vacuo to constant weight giving 1.58 g. of a yellow foam.

G. BocNle-2-N-i-butylazahomocyclohexylStahys(e-CBZ)Sta benzyl ester

Boc-L-norleucine (222 mg.) was coupled with 800 mg. of the product of Example 15F according to the procedure of Example 2H and the product obtained as a colorless foam, 578 mg.

H. Nle-2-N-i-ButylazahomocyclohexylStaLys(e-CBZ)Sta benzyl ester hydrochloride To 5 ml. of 4N hydrogen chlorine-dioxane was added 565 mg. of the product of Example 15G at 25° C. After 45 minutes the mixture was evaporated to dryness, coevaporated several times with ether and dried at 56° C. in vacuo to constant weight yielding 532 mg. colorless powder.

I. BocPheNle-2-N-i-butylazahomocyclohexylStaLys(e-CBZ)Sta benzyl ester

Boc-L-Phe (146 mg.) was coupled to 521 mg. of the product of Example 15H according to the procedure of Example 2H and the analogously isolated title substance was obtained as a colorless foam (513 mg.).

J. BocPheNle-2-N-i-butylazahomocyclohexylStaLysSta

The product of Example 15I, 502 mg., was dissolved in 10 ml. methanol and 1 ml. acetic acid shaken with 20% Pd(OH)$_2$/C (120 mg., Pearlman's catalyst) for 40 minutes at 25° C. and 50 p.s.i. hydrogen. The filtered mixture was evaporated and coevaporated with toluene then with ether to give after drying in vacuo at 56° C. for 2 hours 417 mg. of the title substance as a pale yellow amorphous solid.

NMR (DMSO) 250 mHz, partial, delta: 0.78–0.92 (m, 15H), 1.32 (s, 9H, Boc), 4.3–4.4 (m, 1H), 4.1–4.2 (m, 2H), 6.2 (m, 1H), 7.03 (d, 1H, J=9 Hz), 7.3 (m, aromatic), 7.45, 7.67 and 7.97 (d, 1H, ea, J=8–9 Hz) ppm.

EXAMPLE 16

BocPheHis-2-N-i-butylazahomocyclohexylSta-(N-5-cyanopentyl)amide ($R_1$=H; $R_2$=NH(CH$_2$)$_5$CN; and X=NCH$_2$CH(CH$_3$)$_2$)

A. 5-Cyanopentylisocyanate

6-Aminocapronitrile, 20 g., was dissolved in 125 ml. toluene and excess hydrogen chloride gas was introduced. The resultant suspension was then brought to reflux and maintained under an atmosphere of phosgene until a homogeneous solution resulted (4 hours). The filtered mixture was concentrated by distillation at atmospheric pressure and the residue fractionally distilled at 0.05 mm giving 9.8 g., bp 106°–109° C.

B. N-i-Butyl-N-[3(S)-N-t-butoxycarbonylamino-2(R)-t-butyldimethylsiloxy-4-cyclohexylbut-1-yl]N'-5-cyanopentyl urea The product of Example 8A, 1.6 g., and the product of Example 16A, 0.48 g., were mixed together at 0° C. in 10 ml. dichloromethane. After 15 minutes the mixture was concentrated and chromatographed on silica eluting with ethyl acetate/hexane, giving 1.434 g. of the title substance as a colorless foam.

C. N-i-Butyl N-[3(S)-amino-2(R)-hydroxy-4-cyclohexylbut-1-yl]N'-5-cyanopentyl urea hydrochloride The product of Example 16B, 1.4 g. was dissolved in 6 ml. 4N hydrogen chloride-dioxane at 0° C. and brought to 25° C. The concentrated mixture was coevaporated with ether and brought to constan weight at 56° C. giving 1.05 g. of the title hydrochloride.

D. BocPheHis-2-N-i-butylazahomocyclohexylSta-(N-5-cyanopentyl)amide

The product of Example 16C, 0.504 g., and 0.64 g. BocPheHis(imBoc) were coupled according to the procedure of Example 2H and the analogously isolated product (purified on silica using an ethyl acetate/hexane gradient instead of dichloromethane/ethanol) weighed 593 mg.

E. BocPheHis-2-N-i-butylazahomocyclohexylSta-(N-5-cyanopentyl)amide

The product of Example 16D (575 mg.) was dissolved in 5 ml. methanol and treated with 250 mg.) potassium carbonate. After 20 minutes 1 ml. acetic acid was added and the mixture was concentrated to dryness. The solid was dissolved in a small volume of 1:1 water-methanol and chromatographed on a 5 g. Baker RP-18 silica column first with 3 column volume of 1:1 then with 100:0 methanol-water. The methanol fractions were concentrated and the residue brought to constant weight (391 mg.) in vacuo at 56° C. The title compound was a colorless amorphous foam.

NMR, proton, 300 mHz, CDCl$_3$, partial, delta, 0.95 (two d, 6H total), 1.44 (s, 9H, Boc), 2.40 (t, 2H, J=7 Hz), 3.02 (m, 2H), 3.14 (d, 1H, J=7 Hz), 3.27 (m, 3–4H), 3.69, 3.94, 4.29, 4.63, 5.14 (m, 1H ea), 6.7 (d, 1H, J=9 Hz), 6.93 and 7.90 (s, 1H ea, imidazolyl CH), 7.14–7.5 (m, 6–7H) ppm.

EXAMPLE 17

BocPheHis-2-N-i-butylazahomocyclohexylSta benzyl ester ($R_1$=H; $R_2$=OCH$_2$C$_6$H$_5$; and X=NCH$_2$CH(CH$_3$)$_2$)

A. Benzyl N-isobutyl N-[3-(S)-t-Bocamino-2(R)-t-butyldimethylsilyloxy-4-cyclohexylbut-1-yl]carbamate The product of Example 8A, 2.6 g., was dissolved in 10 ml. dioxane and 5 ml. water and adjusted at 0° C. to pH 11. CBZ-chloride (1.14 ml.) was added and the pH was maintained at 10 to 11 by addition of 6N sodium hydroxide. After 10 minutes the pH stabilized and the mixture was concentrated, dissolved in ethyl acetate, separated and the organic layer was washed with aqueous bicarbonate, brine, dried over magnesium sulfate, filtered and concentrated giving 3.78 g. of a clear oil which was chromatographed on silica eluting with ethyl acetate-hexane to provide 2.42 g. of the title substance as a clear oil.

B. Benzyl N-isobutyl N-[3(S)-amino-2(R)-hydroxy-4-cyclohexylbut-1-yl]carbamate hydrochloride The product of Example 17A (2.32 g.) was dissolved in 4N hydrogen chloride-dioxane and kept there for 30 minutes. The mixture was concentrated, coevaporated several times with ether and dried briefly in vacuo. To the residue was added 10 ml. 1:5 48% aqueous hydrofluoric acid; acetonitrile and the mixture was stirred at 25° C. After 20 minutes 0.5 ml. 48% hydrofluoric acid was added, and after a period of 2 hours another 6 ml. aqueous 48% hydrofluoric acid was added. After a total reaction time of 4 hours, the mixture was treated with solid sodium bicarbonate, concentrated, extracted with dichloromethane, dried, filtered, and concentrated to give 0.82 g. of a yellow oil.

C. BocPheHis(imBoc)-2-N-i-butylazahomocyclohexylSta benzyl ester

The product of Example 17B (0.548 g.) was coupled to 0.768 g. BocPheHis(imBoc) by the procedure of Example 2H, giving after analogous workup and purification 0.60 g. of a colorless foam.

D. BocPheHis-2-N-i-butylazahomocyclohexylSta benzyl ester

The product of Example 17C (0.575 mg.) was treated with potassium carbonate in methanol and the product purified as for the preparation of Example 16E, giving 475 mg. of the title substance as a colorless foam.

NMR, proton, 250 mHz, DMSO, partial, delta, 0.8 (m, 7–9H), 1.32 (s, 9H, Boc), 3.83, 4.16, 4.52, 6.9 and 8.3 (m, 1H ea), 5.08 (AB doublets, 2H, CH$_2$CO$_2$), 7.53 (s, 1H, imidazole 2-H), 7.1–7.43 (m, 6.7H) ppm.

EXAMPLE 18

BocPheHis-2-N-i-butylazahomocyclohexylSta(N-aminohexyl)amide ($R_1$=H; $R_2$=NH(CH$_2$)$_6$NH$_2$; and X=NCH$_2$CH(CH$_3$)$_2$)

The product of Example 16E (267 mg.) was dissolved in methanol (10 ml.) and ammonia was introduced until about 0.5 g. was dissolved, 0.265 g. 5% Rh/C was added and the mixture was shaken under 50 p.s.i. hydrogen at 25° C. for 3.5 hours. Filtration, concentration, coevaporation with ether, and drying to constant weight (254 mg.) produced the title substance, a colorless powder.

NMR, proton, 250 mHz, DMOS, partial, delta, 0.8 (m, 6H, CMe$_2$), 1.28 (s, 9H, Boc), 3.53, 3.87, 4.19 4.48, 5.2, 6.42, 6.75 (m, 1H ea), 6.88 (d, J=9 Hz), 7.46 (s, 1H, imidazolyl 2H), 7.1–7.4 (m, 5–7H) ppm.

EXAMPLE 19

BocPheHis-2-N-i-butylazahomocyclohexylSta[N-2(4-imidazolylethyl)]amide ($R_1$=H; $R_2$=NH(CH$_2$)$_2$C$_3$H$_3$N$_2$; and X=NCH$_2$CH(CH$_3$)$_2$)

A. N-isobutyl N-[3(S)-N-t-butoxycarbonylamino-2(R)-t-butyldimethylsilyloxy-4-cyclohexylbut-1-yl]-N'-2-(4-imidazolyl)ethyl urea 440 mg. Histamine was coupled to 1.5 g. of the product of Example 8A according to the procedure of Example 2F, except that the reaction mixture was maintained at reflux for 48 hours instead of stirring at 25° C. The crude mixture after extraction (sodium bicarbonate solution was used instead of 1N HCl) was chromatographed on silica eluting with an ethanoldichloromethane gradient (increasing ethanol from initial 1%) containing 1% triethylamine to give 606 mg. of the pure title substance.

B. N-isobutyl N-[3(S)-amino-2(R)-hydroxy-4-cyclohexylbut-1-yl]-N'-2-(4-imidazolyl)ethyl urea hydrochloride The product of Example 19A (558 mg.) was dissolved in 8 ml. 4N hydrogen chloride-dioxane for 1 hour at 25° C., concentrated, coevaporated several times with ether, and brought to constant weight at 56° C. giving 480 mg. of the title compound, a yellowish powder.

C.
BocPheHis(imBoc)-2-N-i-butylazahomocyclohexyl-Sta[N-2(4-imidazolylethyl)]amide According to the procedure of Example 2H, 450 mg. of the product of Example 19B was coupled to 525 mg. BocPheHis(imBoc) giving after analogous isolation and purification 421 mg. of the title substance, a colorless amorphous foam. The compound contained 25% of a more polar impurity by RP-HPLC.

D.
BocPheHis-2-N-i-butylazahomocyclohexylSta-(N-4-imidazolylethyl)amide

The product of Example 19C (402 mg.) was treated with potassium carbonate in methanol and the product purified as in Example 16E, giving 361 mg. of the title substance as a colorless foam, contaminated by a more polar impurity which was removed by preparative HPLC, eluting a Dupont Zorbax C-8 250×9.6 mm column at 6.3 mL/min. with 40/60 acetonitrile/pH 4.3 0.1M ammonium acetate buffer, observing at 254 nm, 15 mg. of the above crude material was injected in each pass, and purification of 110 mg. of the crude material gave 50 mg. of pure product after solvent concentration and drying to constant weight.

NMR (DMSO) 250 mHz, partial, delta, 0.8 (d, 6H, J=7 Hz, CMe$_2$), 1.32 (s, 9H, Boc), 3.87, 4.17 and 4.62 (m, 1H ea), 6.43 and 8.36 (m, 1H ea), 6.78 and 6.85 (both s, 2H total), 7.53 (s, 2H, imidazolyl 2H), 7.1–7.4 (m, aromatic, 5–7H) ppm.

EXAMPLE 20

N'-i-Butyl-N-[3(S)-BocPheHisamino-2(R)-hydroxy-4-cyclohexylbut-1-yl]-3-methylbutyramide (R$_1$=H; R$_2$=CH$_2$CH(CH$_3$)$_2$; and X=NCH$_2$CH(CH$_3$)$_2$)

A.
N'-i-Butyl-N-[3(S)-t-Bocamino-2(R)-t-butyldimethylsilyloxy-4-cyclohexylbut-1-yl]-3-methylbutyramide The product of Example 8A (1.23 g.) was dissolved in 9 ml. 1:1 dioxane-water, cooled to 0° C., adjusted to pH 11 with 1N sodium hydroxide and treated with 0.36 ml. isovaleryl chloride. The pH was maintained at 11 and after stabilization occurred (10 minutes) the mixture was concentrated, the residue dissolved in ethyl acetate, separated, the organic layer washed with brine, dried, filtered, concentrated and chromatographed on silica in ethyl acetate-hexane giving 0.89 g. of product as a colorless oil.

B.
N'-i-Butyl-N-[3(S)-amino-2(R)-hydroxy-4-cyclohexylbut1-yl]-3-methylbutyramide hydrochloride The product of Example 20A (0.84 g.) was dissolved for 1 hour in 5 ml. 4N hydrogen chloride-dioxane, concentrated, coevaporated with ether, dried in vacuo 15 minutes, and dissolved at 25° C. in 5 ml. 1:5 48% aqueous hydrofluoric acid/acetonitrile for 1 hour whereupon 1 ml. 48% aqueous hydrofluoric acid was added, and the mixture was stirred another 4 hours. Excess solid sodium bicarbonate was added and the concentrated mixture was extracted with ethyl acetate which was washed with water, dried over magnesium sulfate, filtered, concentrated, and taken to constant weight in vacuo giving 550 mg. of a pale yellow amorphous solid.

C.
N'-i-Butyl-N-[3(S)-BocPheHis(imBoc)amino-2(R)-hydroxy-4-cyclohexylbut-1-yl]-3-methylbutyramide According to the procedure of Example 2H, BocPheHis(imBoc) (0.396 g.) was coupled in dichloromethane to 257 mg. of the product of Example 20B using 109 ul. triethylamine, 181 mg. 1-hydroxybenzotriazole and 162 mg. dicyclohexylcarbodiimide. The analogously isolated product (283 mg.) was a colorless foam.

D.
N'-i-Butyl-N-[3(S)-BocPheHisamino-2(R)-hydroxy-4-cyclohexylbut-1-yl]-3-methylbutyramide The product of Example 20C (272 mg.) was dissolved in 2 ml. methanol and 138 mg. potassium carbonate was added at 25° C. After 30 minutes 0.8 ml. acetic acid was added and the mixture was evaporated to dryness in vacuo. The residue was dissolved in 2 ml. 1:1 acetonitrile/water and chromatographed with the same solvent on 5 g. Baker RP-18 silica, eluting with 3 column volume. Methanol was then used to flush the title substance from the column, giving 218 mg. after drying to constant weight.

NMR (DMSO) 250 mHz, partial, delta: 0.7–0.95 (m, 12H), 3.87, 4.15, 4.53 and 6.88 (m, 1H ea), 7.53 (s, 1H), 7.4–7.1 (m, 5–7H).

EXAMPLE 21

N-Carbomethoxymethyl-N-[3(S)-BocPheHisamino-2(R)-hydroxy-4-cyclohexylbut-1-yl]-3-methylbutyramide (R$_1$=H; R$_2$=CH$_2$CH(CH$_3$)$_2$; and X=NCH$_2$CO$_2$CH$_3$

A.
N-Carbobenzyloxymethyl-N-[3(S)-Bocamino-2(R)-t-butyldimethylsilyloxy-4-cyclohexylbut-1-yl]amine The product of Example 2D (4.81 g.) was heated with 3.14 ml. diisopropylethylamine and 1.90 ml. methyl bromoacetate in 50 ml. dry acetonitrile for 1.2 hours, cooled, concentrated, the residue dissolved in ethyl acetate, which was washed with saturated aqueous bicarbonate (3×40 ml.), dried over magnesium sulfate, filtered, concentrated and chromatographed in ethyl acetate-hexane upon silica giving 3.35 g. of the title amine as a colorless oil.

B.
N-Carbobenzyloxymethyl-N-[3(S)-t-Bocamino-2(R)-t-butyldimethylsilyloxy-4-cyclohexylbut-1-yl]-3-methylbutyramide The product of Example 21A (1.15 g.) was dissolved in 5 ml. dichloromethane with 0.36 ml. 2,6-lutidine at 0° C. and treated dropwise with 0.255 ml. isovaleryl chloride. The mixture was then washed with 1N hydrochloric acid (2×5 ml.), saturated aqueous sodium bicarbonate, dried, filtered, concentrated, giving 1.23 g. of a colorless foam used without further purification.

C. N-Carbobenzyloxymethyl N-[3(S)-amino-2(R)-hydroxy-4-cyclohexylbut-1-yl] 3-methylbutyramide hydrochloride The product of Example 21B (1.12 g.) was dissolved in 5 ml. 1:10 aqueous 48% hydrofluoric acid/acetonitrile at 0° C., brought to 25° C., and stirred for 1 hour. A saturated aqueous sodium bicarbonate solution (4 ml.) was added and the concentrated residue extracted with ethyl acetate, which was washed with bicarbonate, water, dried over magnesium sulfate, filtered, concentrated and dissolved in 4 ml. 4N hydrogen chloridedioxane. After being stirred at 25° C. for 1 hour the mixture was concentrated and dried to constant weight giving 705 mg. of a yellow foam.

D.
N-Carbobenzyloxymethyl-N-[3(S)-BocPheHis(imBoc)-amino-2(R)-hydroxy-4-cyclohexylbut-1-yl]-3-methylbutyramide According to the procedure of Example 2H, 769 mg. of the product of Example 21C was neutralized with triethylamine (0.305 ml.) in dichloromethane (5 ml.) at 0° C., and coupled to 850 mg. BocPheHis(imBoc) using 389 mg. 1-hydroxybenzotriazole and 349 mg. dicyclohexylcarbodiimide. The analogously isolated and purified title substance weighed 784 mg.

E.
N-Carbomethoxymethyl-N-[3(S)-BocPheHisamino-2(R)-hydroxy-4-cyclohexyl-1-yl]-3-methylbutyramide The product of Example 21D (125 mg.) was dissolved in 0.5 ml. methanol and 4 mg. potassium carbonate was added. After 40 minutes 100 ul. acetic acid was added and the concentrate was dissolved in 1:1 methanol-water and chromatographed in the same on 5 g. Baker RP-2 gel eluting with 2 column volume. The column was then eluted 2 column volume of methanol and the latter was concentrated giving 86 mg. of the transesterified title substance as a colorless solid.

NMR (DMSO) 250 mHz, partial, delta, 0.94 (m, 6H), 1.36 and 1.38 (s, 9H total, Boc, 2 discrete conformers), 4.54 and 5.15 (m, 1H ea), 7.1–7.4 (m, 5–6H), 7.62 (s, 1H) ppm.

EXAMPLE 22

BocPheHis-2-N-i-butylazahomocyclohexylSta amide ($R_1$=H; $R_2$=NH$_2$; and X=NCH$_2$CH(CH$_3$)$_2$)

A.
N-Isobutyl-N-[3-(S)-t-Bocamino-2(R)-t-butyldimethylsilyloxy-4-cyclohexylbut-1-yl]urea The product of Example 8A (792 mg.) was dissolved in 5 ml. dichloromethane and treated with 1.3 ml. trimethylsilyl isocyanate. The mixture was stirred overnight and 0.65 ml. acetic acid was added. The concentrate (0.906 g.) was chromatographed on silica eluting with ethyl acetate-hexane, giving after solvent removal 327 mg. of the pure urea.

B.
N-isobutyl-N-[3(S)-amino-2(R)-hydroxy-4-cyclohexylbut-1-yl] urea hydrochloride The product of Example 22A (313 mg.) was dissolved in 5/95 aqueous 48% hydrofluoric acid/acetonitrile (5 ml.) for 2 hours. Sodium bicarbonate was added, and the concentrated mixture was extracted with ethyl acetate which was washed with water, dried over magnesium sulfate, filtered, concentrated, giving 242 mg. of a colorless foam which was dissolved for 45 minutes in 5 ml. 4N hydrogen chloride-dioxane at 25° C., concentrated, coevaporated with ether several times and brought to constant weight in vacuo giving 208 mg. of a yellow powder.

C.
BocPheHis(imBoc)-2-N-i-butylazahomocyclohexylSta amide

The product of Example 22B, (196 mg.) triethylamine-neutralized, was coupled to 308 mg. BocPheHis(imBoc) according to the general procedure of Example 2H and the analogously isolated and purified title substance was a colorless foam, weight 248 mg.

D. BocPheHis-2-N-i-butylazahomocyclohexyl Sta amide

The product of Example 22E (232 mg.) was dissolved in 4 ml. methanol and treated with 40 mg. potassium carbonate at 25° C. for 15 minutes. Acetic acid (0.25 ml.) was added and the mixture was concentrated, dissolved in 1:1 methanol-water, and chromatographed in the same (2 column volume) on a 5 g. column of Baker RP-18 resin. Methanol was then used to elute the column, and the methanol fractions concentrated gave after drying in vacuo 178 mg. of the pure title substance.

NMR (DMSO) 250 mHz, partial, delta, 0.76 (d, 6H), 1.30 (s, Boc, 9H), 3.58, 3.84, 4.12, 4.50 and 5.36 (m, 1H ea), 5.78 (br, 2H), 6.88 and 7.52 (s, 1H ea, imidazolyl CH), 7.1–7.4 (m, 5–6H) ppm.

EXAMPLE 23

BocPheHis-2-N-benzylazahomocyclohexylSta methylamide ($R_1$=H; $R_2$=NHCH$_3$; and X=NCH$_2$C$_6$H$_5$)

A.
N-Benzyl-3(S)-N-t-butoxycarbonylamino-2(R)-t-butyldimethylsilyloxy-4-cyclohexyl-1-butylamine The product of Example 2D (0.56 g.) was dissolved in 3 ml. methanol containing 0.4 ml. acetic acid and 200 mg. 600 mesh 3A sieves were added, followed by sodium cyanoborohydride (0.097 g.), and the mixture was stirred at 25° C. while 0.16 ml. benzaldehyde was added over 2 minutes. After 5 minutes the mixture was filtered, concentrated, dissolved in ethyl acetate, washed with bicarbonate solution, water, brine and dried. Solvent removal gave 0.71 g. of a colorless oil which was not further purified.

B.
N-Benzyl-N-[3(S)-N-t-butoxycarbonylamino-2(R)-t-butyldimethylsilyloxy-4-cyclohexyl-but-1-yl]-N'-methyl urea A solution of 0.70 g. of the product from Example 23A in methylene chloride (3 ml.) was treated with 0.084 ml. methyl isocyanate and after 15 minutes the mixture was concentrated, chromatographed on silica eluting with 15%, then 33% ethyl acetate in hexane. The pure material was consolidated and evaporated giving 0.54 g. of the title substance as a colorless foam.

C.
N'-Benzyl-N-[3(S)-amino-2(R)-hydroxy-4-cyclohexylbut-1-yl] N'-methyl urea hydrochloride The product from Example 23B (0.52 g.) was dissolved in 4N hydrogen chloride-dioxane at 25° C. and stirred for 1 hour. The mixture was concentrated and the residue coevaporated with ether giving after drying to constant weight 0.4 g. of a pale yellow powder used below without purification.

D. BocPheHis(imBoc)-2-N-benzylazahomocyclohexylSta methylamide

According to the procedure of Example 2H, the product of Example 23C was neutralized with triethylamine and coupled to BocPheHis(imBoc) using dicyclohexylcarbodiimide and 1-hydroxybenzotriazole, giving after analogous isolation 618 mg. of the title substance.

E. BocPheHis-2-N-benzylazahomocyclohexylSta methylamide

The product of Example 23D (608 mg.) was dissolved in 5 ml. 80% aqueous acetic acid and stirred at 25° C. for 15 hours. The mixture was concentrated to a colorless powder, which was triturated with 2:1 dichloromethane-ether, and the insoluble material, 281 mg. was pure by RP-HPLC, giving the following NMR data.

$^1$H-NMR, DMSO, 300 mHz, ppm from TMS, partial: 1.28 (s, 9H, Boc), 2.58 (d, 3H), 4.46 (s, 2H), 3.55, 3.80, 4.10, 5.44 and 6.32 (m, 1H, ea), 6.82 and 7.48 (s, 1H ea, imidazolyl C-2), 7.1–7.4 (m, aromatic) ppm.

PREPARATION A

N-t-Butoxycarbonyl-L-phenylalanyl-L-N(im)-t-butoxycarbonyl-histidine (BocPheHis(imBoc))

A. Boc-L-phenylalanyl-L-histidine methyl ester

A slurry of 36.4 g. L-histidine methyl ester dihydrochloride in dichloromethane (1 l.) was cooled to 5° C. and treated with 52 ml. triethylamine. After 10 minutes 40 g. Boc-L-phenylalanine was added followed by 1-hydroxybenzotriazole (30.6 g.), then after another 5 minutes by dicyclohexylcarbodiimide (30.8 g.), and the mixture was stirred at 0° C. for 4 hours and at 20° C. for 90 hours. The mixture was then filtered and the filtered solid was washed with dichloromethane, and the combined organic layers were concentrated and the residue was dissolved in 1 l. ethyl acetate. After 10 minutes of stirring the mixture was filtered and the filtrate was washed with 1N sodium hydroxide (3×150 ml.), brine, dried over magnesium sulfate and concentrated giving 45.9 g. of a colorless solid which was used without additional purification in Step B.

B. BocPheHis(imBoc)

Forty grams of the solid produced in Step A was dissolved in 600 ml. methanol and 200 ml. water was added. The chilled (0° C.) mixture was treated with 40 g. anhydrous potassium carbonate, stirred at 15°–20° C. for 2.5 hours, then at 28° C. for 1.5 hours, cooled to 10° C., and adjusted to pH 4.2 with 12N hydrochloric acid. The above solution was concentrated to about 250 ml. and 70 ml. water was added followed by 660 ml. dioxane. The pH was brought at 0° C. to 13.5 and 29 ml. di-t-butyldicarbonate was added. After 0.5 hour (during which time the temperature was raised to 20° C.) the pH had dropped to 9.5 and 10 ml. di-t-butyldicarbonate was added. After 1 hour the pH was 8.0 and the reaction was complete as measured by RP-HPLC. The mixture was concentrated to remove dioxane, 300 ml. water was added, and the mixture was washed twice with ether, 500 ml. ethyl acetate was added and the pH was brought at 10° C. to 1.2 with concentrated hydrochloric acid. The organic layer was separated and the aqueous layer was washed twice with ethyl acetate. The ethyl acetate layers were combined, washed with water, brine, dried over sodium sulfate, and concentrated to give after several coevaporations with ether and drying at 25° C. to constant weight a colorless foam, weight 44 g. HPLC at 60/40 acetonitrile/pH 2.1 0.1M phosphate on Zorbax 25 cm×4.6 mm at 214 nm, 1.5 ml/min retention time 3.23 (94% of the total absorbence to 10 minutes).

PREPARATION B

N-(2-t-Butoxycarbonylamino-3-methyl-n-pentyl)-L-phenylalanine benzyl ester (BocIleRPhe benzyl ester)

A. N-(t-butoxycarbonyl)-L-Isoleucinal

A mixture of L-isoleucine methyl ester (24.3 g., 0.134 mmoles) and triethylamine (13.5 g., 0.134 mmoles) in methylene chloride (210 ml.) was prepared and a solution of ditertbutyldicarbonate (Aldrich, 29.1 g., 0.134 mmoles) in methylene chloride (25 ml.) was added dropwise to this mixture at 0° C. After completion of this addition, the mixture was allowed to warm to room temperature overnight and was then filtered. The filtrate was washed successively with water (1×100 ml.) and a saturated sodium bicarbonate solution (1×75 ml.), dried over magnesium sulfate and evaporated to yield N-(t-butoxycarbonyl)-L-isoleucine methyl ester as an oil [30.7 g.; 93% yield; $^1$H-NMR (CDCl$_3$): delta 0.92 (d, J=7,6H), 1.43 (s, 9H), 3.70 (s, 3H), 4.17 (dd, J=5, 9, 1H), 5.03 (d, J=9, 1H)]. A solution of the N-(t-butoxycarbonyl)-L-isoleucine methyl ester oil (15.0 g., 61.1 mmoles) in dry toluene (260 ml.) was cooled to −78° C., and a 1M solution of diisobutyl aluminum hydride in hexane (153 ml.) was added dropwise thereto at such a rate that the temperature of the exothermic reaction did not exceed −65° C. Following 15 minutes of addition stirring at −78° C. after completion of this addition, the mixture was carefully quenched with 15 ml. of methanol (the mixture temperature was not allowed to exceed −65° C.) followed by 200 ml. of Rochelle salt solution. After warming to room temperature, the organic layer was separated and extracted with ether (3×200 ml.); additional Rochelle salt solution was added when necessary to dissolve the aluminum salts. The combined organic extract was dried over sodium sulfate and evaporated to afford a crude product as an oil. The oil was stored at −78° C. to avoid possible racemization and was used without purification in the next step [132 g., 98% yield, Rf=0.32 in 35% ether in hexane; $^1$H-NMR (CDCl$_3$): delta 1.00 (d, J=7,6H), 1.46 (s, 9H), 9.65 (s, 1H)].

B. N-(2-t-butoxycarbonylamino-3-methyl-n-pentyl)-L-phenylalanine benzyl ester A mixture of N-(t-butoxycarbonyl)-L-isoleucinal (2.0 g., 9.29 mmoles) and L-phenylalanine benzyl ester p-tosylate (3.78 g., 8.84 mmoles) in 150 ml. methanol was stirred for 35 minutes in the presence of 3 Angstrom molecular sieve at room temperature. Sodium cyanoborohydride (730 mg., 11.6 mmoles) was then added and the mixture was stirred for another 1 hour at room temperature. The sieves were then filtered off and the filtrate concentrated to an oil residue, which was diluted with saturated aqueous sodium bicarboante solution and extracted twice with ether. The combined ether extract was dried over sodium sulfate and concentrated to an oil which was purified by flash chromatography using 12% ethyl acetate in hexane as eluent to afford 1.69 g. (40% yield) of the desired intermediate, m.p. 53°–55°.
$^1$H-NMR (CDCl$_3$): 0.6–1.0 (m, 6H), 1.48 (s, 9H), 2.92 (d, J=7,2H), 5.07 (s, 2H), 7.17 (s, 5H), 7.25 (s, 5H)] ppm.
I claim:
1. A compound of the formula
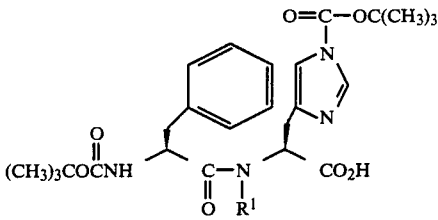
wherein R$^1$ is selected from the group consisting of hydrogen and methyl.
2. The compound of claim 1, wherein R$^1$ is hydrogen.
3. The compound of claim 1, wherein R$^1$ is methyl.
* * * * *